(12) United States Patent
Wu

(10) Patent No.: US 9,598,365 B2
(45) Date of Patent: Mar. 21, 2017

(54) **METHOD FOR SYNTHESIZING CYCLOALKANYL[*B*]INDOLES, CYCLOALKANYL[*B*]BENZOFURANS, CYCLOALKANYL[*B*]BENZOTHIOPHENES, COMPOUNDS AND METHODS OF USE**

(71) Applicant: Trustees of Dartmouth College, Hanover, NH (US)

(72) Inventor: Jimmy Wu, Hanover, NH (US)

(73) Assignee: TRUSTEES OF DARTMOUTH COLLEGE, Hanover, NH (US)

( * ) Notice: Subject to any disclaimer, the term of this patent is extended or adjusted under 35 U.S.C. 154(b) by 0 days.

(21) Appl. No.: 14/537,154

(22) Filed: Nov. 10, 2014

(65) Prior Publication Data
US 2015/0057326 A1 Feb. 26, 2015

Related U.S. Application Data

(63) Continuation-in-part of application No. PCT/US2013/042148, filed on May 22, 2013.

(60) Provisional application No. 61/757,876, filed on Jan. 29, 2013, provisional application No. 61/650,039, filed on May 22, 2012.

(51) Int. Cl.
| | | |
|---|---|---|
| C07D 209/70 | (2006.01) |
| C07D 405/04 | (2006.01) |
| C07D 409/04 | (2006.01) |
| A61K 31/403 | (2006.01) |
| C07D 209/94 | (2006.01) |
| C07D 209/96 | (2006.01) |
| C07D 491/08 | (2006.01) |
| C07D 491/18 | (2006.01) |

(52) U.S. Cl.
CPC ......... *C07D 209/94* (2013.01); *C07D 209/70* (2013.01); *C07D 209/96* (2013.01); *C07D 405/04* (2013.01); *C07D 409/04* (2013.01); *C07D 491/08* (2013.01); *C07D 491/18* (2013.01)

(58) Field of Classification Search
None
See application file for complete search history.

(56) References Cited

U.S. PATENT DOCUMENTS

| | | | |
|---|---|---|---|
| 2007/0037791 A1 | 2/2007 | Rawson et al. | 514/215 |
| 2008/0027090 A1 | 1/2008 | Wilson et al. | 514/289 |
| 2009/0156621 A1 | 6/2009 | Gudmundsson | 514/275 |
| 2009/0170923 A1 | 7/2009 | Gudmundsson | 514/411 |
| 2011/0003737 A1 | 1/2011 | Guzzo et al. | 514/5.3 |
| 2011/0152306 A1 | 6/2011 | Shi et al. | 514/286 |

FOREIGN PATENT DOCUMENTS

| | | |
|---|---|---|
| EP | 1184373 A1 | 3/2002 |
| EP | 1505061 A1 | 2/2005 |
| JP | 2010135689 A * | 6/2010 |
| WO | WO 03/091257 A1 | 11/2003 |
| WO | WO 2004/063156 A1 | 7/2004 |
| WO | WO 2004/069831 A1 | 8/2004 |
| WO | WO 2004/110999 A1 | 12/2004 |
| WO | WO 2005/023245 A1 | 3/2005 |
| WO | WO 2005/094833 A1 | 10/2005 |
| WO | WO 2006/034090 A1 | 3/2006 |
| WO | WO 2006/047017 A1 | 5/2006 |
| WO | WO 2006/055760 A1 | 5/2006 |
| WO | WO 2008/021364 A2 | 2/2008 |
| WO | WO 2009/120720 A1 | 10/2009 |
| WO | WO 2010/036998 A2 | 4/2010 |
| WO | WO 2010/054382 A1 | 5/2010 |
| WO | WO 2010/111483 A1 | 9/2010 |
| WO | WO 2011/044134 A1 | 4/2011 |

OTHER PUBLICATIONS

Solomon, et al., Mol. Cel. Biol., 26:28 (2006).*
Ziegler, et al., J. Org. Chem., 36:1759 (1971).*
Ferreira, et al., JACS, 125:9578 (2003).*
Olson, et al., Org. Lett., 10:573 (Jan. 24, 2008).*
Eitel, et al., J. Org. Chem., 55:5368 (1990).*
CAS Registry, RN 1259490-41-9, Entered STN Jan. 18, 2011.*
Ambekar, S. Y. "Recent Developments in the Fischer Indole Synthesis" Current Science 1983 52(12):578-582.
Aungst, R. A. Jr. and Funk, R. L. "Stereoselective Preparation of (Z)-2-(Trialkylsilyloxy)-2-alkenals by Retrocycloaddition Reactions of 4*H*-4-Alkyl-5-(trialkylsilyloxy)-1,3-dioxins. Useful Reactants for Lewis Acid Catalyzed [4+3] Cyclizations" Organic Letters 2001 3(22) :3553-3555.
Barf et al. "N-Benzyl-Indolo Carboxylic Acids: Design and Synthesis of Potent and Selective Adipocyte Fatty-Acid Binding Protein (A-FABP) Inhibitors" Bioorganic & Medicinal Chemistry Letters 2009 19:1745-1748.
Barluenga et al. "The Azaallylic Anion as a Synthon for Pd-Catalyzed Synthesis of Heterocycles: Domino Two- and Three-Component Synthesis of Indoles" Angewandte Chemie International Edition 2007 46:1529-1532.
Battiste et al. "The Cycloaddition Strategy for the Synthesis of Natural Products Containing Carbocyclic Seven-Membered Rings" Chemistry A European Journal 2006 12:3438-3447.

(Continued)

*Primary Examiner* — Michael Barker
(74) *Attorney, Agent, or Firm* — David F. Cauble; Lathrop & Gage LLP

(57) ABSTRACT

A method of synthesizing cycloalkanyl[b]indoles, as well as related cycloalkanyl[b]benzofurans and cycloalkanyl[b]benzothiophenes is provided. The method is a single, multicomponent reaction that combines (1) an indole, benzofuran, or benzothiopene, (2) an aldehyde, ketone, or ketal, and (3) a diene in the presence of an acid, in particular a Ga(III) or In(III) salt. Compositions and methods of using these compounds to stimulate secretion and/or production of glucagon-like peptide-1 or inhibit the activity of Calcitonin Gene-Related Peptide receptor are also provided.

21 Claims, No Drawings

(56) References Cited

OTHER PUBLICATIONS

Blackburn et al. "Lewis Acid Complexes of 1,2-Diketones and their Derivatives. The Synthesis of Seven-Membered Rings" Canadian Journal of Chemistry 1983 61:1981-1986.
Chung et al. "Inter- and Intramolecular [4+3] Cycloadditions Using Epoxy Enol Silanes as Functionalized Oxyallyl Cation Precursors" Journal of the American Chemical Society 2009 131:4556-4557.
Davies, H. M. L. and Dai, X. "Lewis Acid Induced Tandem Diels-Alder Reaction/Ring Expansion as an Equivalent of a [4+3] Cycloaddition" Journal of the American Chemical Society 2004 126:2692-2693.
Hardinger et al. "Bis(sulfonyl) Ketones: A New Oxyallyl Cation Source" The Journal of Organic Chemistry 1995 60:1104-1105.
Harmata, M. "Intramolecular Cycloaddition Reactions of Allylic Cations" Tetrahedron 1997 53(18):6235-6280.
Harmata, M. "Exploration of Fundamental and Synthetic Aspects of the Intramolecular 4+3 Cycloaddition Reaction" Accounts of Chemical Research 2001 34(7):595-605.
Harmata, M. "Asymmetric Catalytic [4+3] Cycloaddition Reactions" Advanced Synthesis & Catalysis 2006 348:2297-2306.
Harmata, M. "The (4+3)—Cycloaddition Reaction: Simple Allylic Cations as Dienophiles" Chemical Communications 2010 46:8886-8903.
Harmata, M. "The (4+3)—Cycloaddition Reaction: Heteroatom-Substituted Allylic Cations as Dienophiles" Chemical Communications 2010 46:8904-8922.
Harmata, M. and Gamlath, C. B. "Intramolecular 4+3 Cycloadditions of 2-Alkoxyallylic Cations from 2-Alkoxyallylic Sulfones" The Journal of Organic Chemistry 1988 53:6154-6156.
Harmata, M. and Wacharasindhu, S. "The [4+3]—Cycloaddition/Quasi-Favorskii Process. Synthesis of the Carbocyclic Core of Tricycloclavulone" Organic Letters 2005 7(13):2563-2565.
Harmata et al. "Intramolecular 4+3 Cycloadditions. Cycloaddition Reactions of Cyclic Alkoxyallylic and Oxyallylic Cations" Journal of the American Chemical Society 1996 118:2860-2871.
Harmata et al. "Intramolecular [4+3] Cycloadditions. Towards a Synthesis of Widdrol" Heterocycles 2004 62:583-618.
Hartung, I. V. and Hoffmann, H. M. R. "8-Oxabicyclo[3.2.1.]oct-6-en-3-ones: Application to the Asymmetric Synthesis of Polyoxygenated Building Blocks" Angewandte Chemie International Edition 2004 43:1934-1949.
Han et al. "Gallium(III)-Catalyzed Three-Component (4+3) Cycloaddition Reactions" Angewandte Chemie International Edition 2012 51:10390-10393.
Inman, M. and Moody, C. J. "A Two Step Route to Indoles from Haloarenes-a Versatile Variation on the Fischer Indole Synthesis" Chemical Communications 2011 47:788-790.
Iovel et al. "Hydroxymethylation of Furan and its Derivatives in the Presence of Cation-Exchange Resins" Journal of Molecular Catalysis 1989 57:91-103.
Ishikura, M. and Kato, H. "A Synthetic Use of the Intramolecular Alkyl Migration Process in Indolylborates for Intramolecular Cyclization: a Novel Construction of Carbazole Derivatives" Tetrahedron 2002 58:9827-9838.
Jeffrey et al. "Generation and Reactivity of Aza-Oxyallyl Cationic Intermediates: Aza-[4+3] Cycloaddition Reactions for Heterocycle Synthesis" Journal of the American Chemical Society 2011 133:7688-7691.
Kuehm-Caubère et al. "Novel Thiopyrano[3,2-*b*] and Cycloalkeno[1,2-*b*]Indole Derivatives with High Inhibitory Properties in LTB$_4$ Production" European Journal of Medicinal Chemistry 1999 34:51-61.
Lee, J. C. and Cha, J. K. "Total Synthesis of (−)—Colchicine by an Oxyallyl [4+3] Cycloaddition" Tetrahedron 2000 56:10175-10184.
Lee, J. C. and Cha, J. K. "Total Synthesis of Tropoloisoquinolines: Imerubrine, Isoimerubrine, and Grandirubrine" Journal of the American Chemical Society 2001 123:3243-3246.
Lee, K. and Cha, J. K. "A New Approach to Phorbol by [4+3] Oxyallyl Cycloaddition and Intramolecular Heck Reaction" Organic Letters 1999 1(3):523-525.
Lee et al. "Total Synthesis of Colchicine. α-Methoxy-Substituted Oxyallyl [4+3] Cycloaddition Approach" The Journal of Organic Chemistry 1998 63:2804-2805.
Liu, L. L. and Chiu, P. "An Expeditious Asymmetric Synthesis of the Pentacyclic Core of the Cortistatins by an Intramolecular (4+3) Cycloaddition" Chemical Communications 2011 47:3416-3417.
Liu, C. and Widenhoefer, R. A. "Palladium-Catalyzed Cyclization/Carboalkoxylation of Alkenyl Indoles" Journal of the American Chemical Society 2004 126:10250-10251.
Lohse, A. G. and Hsung, R. P. "(4+3) Cycloadditions of Nitrogen-Stabilized Oxyallyl Cations" Chemistry 2011 17(14):3812-3822.
Lohse et al. "Developing a Diastereoselective Intramolecular [4+3] Cycloaddition of Nitrogen-Stabilized Oxyallyl Cations Derived from N-Sulfonyl-Substituted Allenamides" The Journal of Organic Chemistry 2011 76(9):3246-3257.
Napper et al. "Discovery of Indoles as Potent and Selective Inhibitors of the Deacetylase SIRT1" Journal of Medicinal Chemistry 2005 48:8045-8054.
Nilson, M. G. and Funk, R. L. "Total Synthesis of (±)—Cortistatin J from Furan" Journal of the American Chemical Society 2011 133(32):12451-12453.
Ragains, J. R. and Winkler, J. D. "Pseudosymmetry in Azabicyclo[2.1.1]hexanes. A Stereoselective Construction of the Bicyclic Core of Peduncularine" Organic Letters 2006 8(20):4437-4440.
Robinson, B. "Recent Studies on the Fischer Indole Synthesis" Chemical Reviews 1969 69(2):227-246.
Sasaki, T. "Catalyzed Cycloaddition Reactions of α-Silyloxy-α,β-Unsaturated Ketone and Aldehyde" Tetrahedron Letters 1982 23(16):1693-1696.
Silvanus et al. "Stereoselective Double Friedel-Crafts Alkylation of Indoles with Divinyl Ketones" Organic Letters 2009 11(5):1175-1178.
Sun et al. "Rhodium-Catalyzed Synthesis of 2,3-Disubstituted Indoles from β, β-Disubstituted Stryryl Azides" Angewandte Chemie International Edition 2011 50:1702-1706.
Willis et al. "Palladium-Catalyzed Tandem Alkenyl and Aryl C—N Bond Formation: A Cascade N-Annulation Route to 1-Functionalized Indoles" Angewandte Chemie International Edition 2005 44:403-406.
Winne et al. "Scope and Mechanism of the (4+3) Cycloaddition Reaction of Furfuryl Cations" Angewandte Chemie International Edition 2011 50:11990-11993.
Xiong et al. "Stereoselective Intramolecular [4+3] Cycloadditions of Nitrogen-Stabilized Chiral Oxyallyl Cations via Epoxidation of N-Tethered Allenamides" Journal of the American Chemical Society 2003 125:12694-12695.
Yu et al. "Concise Synthesis of the Oxapentacyclic Core of Cortistatin A" Organic Letters 2010 12(22):5135-5137.
International Search Report from PCT/US2013/042148, Oct. 18, 2013, PCT.
International Preliminary Report on Patentability from PCT/US2013/042148, Nov. 25, 2014, PCT.
Partial European Search Report corresponding to European Patent Application No. 13794752.9, dated Jun. 1, 2016, 10 pages.
Kazuyuki, Shibata; "Organic White Electroluminescent Devices" Chemical Abstracts Service, Columbus, Ohio; Database accession No. 2010:751949; Fuji Photo Film Co., Ltd. Jun. 17, 2010.
Ivanova et al.; "Lewis Acid-Catalyzed [3+4] Annulation of 2-(Heteroaryl)-cyclopropano-1,1-dicarboxylates with Cyclopentadiene"; Advanced Synthesis & Catalysis, vol. 353, No. 7, May 3, 2011; pp. 1125-1134.

* cited by examiner

METHOD FOR SYNTHESIZING CYCLOALKANYL[B]INDOLES, CYCLOALKANYL[B]BENZOFURANS, CYCLOALKANYL[B]BENZOTHIOPHENES, COMPOUNDS AND METHODS OF USE

INTRODUCTION

This application is a continuation-in-part application of PCT/US2013/042148, filed May 22, 2013, which claims the benefit of priority from U.S. Patent Application Ser. No. 61/650,039, filed May 22, 2012, and 61/757,876, filed Jan. 29, 2013, the contents of which are incorporated herein by reference in their entireties.

BACKGROUND OF THE INVENTION

Cyclohepta[b]indoles (1) exhibit a broad spectrum of biological activity. For instance, compound 2 is a potent inhibitor ($IC_{50}$=63 nM) of SIRT1, a member of the class III histone deacetylases (HDAC; Napper, et al. (2005) *J. Med. Chem.* 48:8045). SIRT1 can effectively deacetylate p53 and has also been implicated in the regulation of apoptosis. With an $IC_{50}$ of 100 nM, compound 3 inhibits the production of leukotriene $B_4$ ($LTB_4$), which is involved in various inflammatory responses (Kuehm-Caubère, et al. (1999) *Eur. J. Med. Chem.* 34:51). A third molecule, compound 4, inhibits adipocyte fatty-acid binding protein (A-FABP) with an $IC_{50}$ of 450 nM (Barf, et al. (2009) *Bioorg. Med. Chem. Lett.* 19:1745).

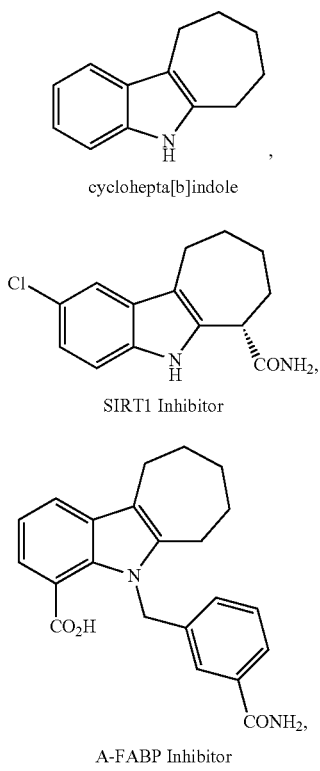

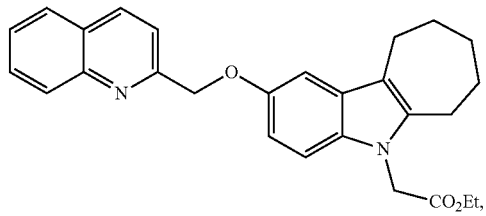

LTB$_4$ Production Inhibitor

The biology of cyclohepta[b]indoles, as well as cyclopenta- and cyclohexa[b]indoles, has attracted considerable interest from the pharmaceutical industry as potential therapeutics. In this respect, various compounds with this structural motif have been described. See, e.g., WO 2010/036998, US 2011/0152306, US 2009/0170923, US 2009/0156621, WO 2004/063156, WO 2010/054382, WO 2006/047017, WO 2006/034090, WO 2004/069831, EP 1184373, WO 2009/120720, WO 2005/023245, WO 2004/110999, WO 2005/094833, WO 03/091257, US 2008/0027090, WO 2011/044134, US 2011/0003737, WO 2010/111483, US 2007/0037791, EP 1505061, WO 2006/055760 and WO 2008/021364.

The preparation of cycloalka[b]indoles often includes the Fisher indole synthesis which, while quite useful, possesses certain limitations (Ambekar (1983) *Curr. Sci.* 52:578; Robinson (1969) *Chem. Rev.* 69:227; Inman & Moody (2011) *Chem. Commun.* 47:788). These include the need to make the requisite hydrazine and ketone starting materials. Regioselectivity with unsymmetrical ketones can also be problematic. Finally, electron-withdrawing groups on the aromatic hydrazine can substantially attenuate reactivity. Other methods for preparing cycloalka[b]indoles are known but have not been extensively explored (Willis, et al. (2005) *Angew. Chem. Int. Ed.* 44:403; Barluenga, et al. (2007) *Angew. Chem. Int. Ed.* 46:1529; Sun, et al. (2011) *Angew. Chem. Int. Ed.* 50:1702; Liu & Widenhoefer (2004) *J. Am. Chem. Soc.* 126:10250; Ragains & Winkler (2006) *Org. Lett.* 8:4437; Silvanus, et al. (2009) *Org. Lett.* 11:1175; Ishikura & Kato (2002) *Tetrahedron* 58:9827).

(4+3) Cycloaddition reactions have been explored in some detail (Harmata (2010) *Chem. Comm.* 46:8886; Harmata (2001) *Acc. Chem. Res.* 34:595; Harmata (2006) *Adv. Synth. Catal.* 348:2297; Battiste, et al. (2006) *Chem. Eur. J.* 12:3438; Hartung & Hoffman (2004) *Angew. Chem., Int. Ed.* 43:1934; Harmata (1997) *Tetrahedron* 53:6235; Chung, et al. (2009) *J. Am. Chem. Soc.* 131:4556; Harmata, et al. (1996) *J. Am. Chem. Soc.* 118:2860; Nilson & Funk (2011) *J. Am. Chem. Soc.* 133:12451; Yu, et al. (2010) *Org. Lett.* 12:5135; Liu & Chiu (2011) *Chem. Commun.* 47:3416; Lee, et al. (1998) *J. Org. Chem.* 63:2804; Lee & Cha (2000) *Tetrahedron* 56:10175; Davies & Dai (2004) *J. Am. Chem. Soc.* 126:2692). A stabilizing group is usually present at C2 of the 2π component (Scheme 1).

SCHEME 1

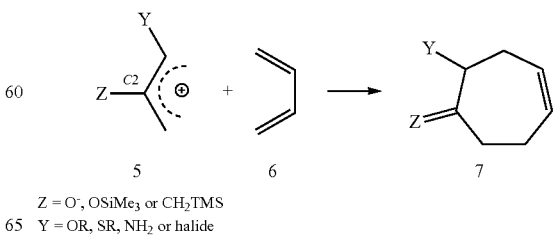

Z = O⁻, OSiMe$_3$ or CH$_2$TMS
Y = OR, SR, NH$_2$ or halide

Heteroatom substitution with sulfur, oxygen, and halide at the terminal ends of the allylic cation are known (Xiong, et al. (2003) *J. Am. Chem. Soc.* 125:12694; Lohse & Hsung (2011) *Chem. Eur. J.* 17:3812; Lohse, et al. (2011) *J. Org. Chem.* 76:3246; Harmata (2010) *Chem. Commun.* 46:8904; Jeffrey, et al. (2011) *J. Am. Chem. Soc.* 133:7688; Lee & Cha (2001) *J. Am. Chem. Soc.* 123:3243; Aungst, Jr. & Funk (2001) *Org. Lett.* 3:3553; Harmata & Wacharasindhu (2005) *Org. Lett.* 7:2563; Lee & Cha (1999) *Org. Lett.* 1:523; Blackburn, et al. (1983) *Can. J. Chem.* 61:1981; Harmata, et al. (2004) *Heterocycles* 62:583; Harmata & Gamlath (1988) *J. Org. Chem.* 53:6154; Hardinger, et al. (1995) *J. Org. Chem.* 60:1104; Sasaki, et al. (1982) *Tetrahedron Lett.* 23:1693). However, cycloaddition reactions utilizing substrates with nitrogen-based substituents have are rare (Xiong, et al. (2003) *J. Am. Chem. Soc.* 125:12694; Lohse & Hsung (2011) *Chem. Eur.* 17:3812; Lohse, et al. (2011) *J. Org. Chem.* 76:3246).

SUMMARY OF THE INVENTION

This invention is a method of synthesizing a cycloalkanyl[b]indole, cycloalkanyl[b]benzofuran or cycloalkanyl[b]benzothiophene by combining, in a single reaction, (a) an indole, benzofuran or benzothiophene; (b) a ketone, aldehyde or ketal; and (c) a coupling partner and adding an acid catalyst thereby producing a cycloalkanyl compounds of Formula Va, Vb, Vc or Vd.

Formula Va
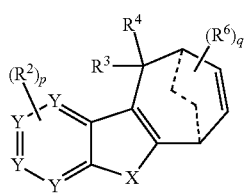

Formula Vb
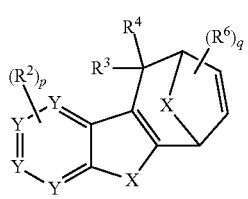

Formula Vc
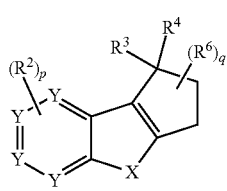

Formula Vd
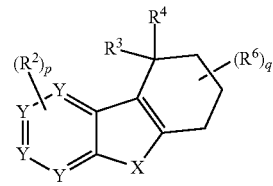

In certain embodiments, the acid catalyst is a Lewis acid, e.g., a metal halide or triflate salt of Ga(III) or In(III); a chiral Lewis acid complex; a Brønsted acid; a chiral phosphoric acid; or other chiral Brøonsted acid.

A compound of Formula Ve, Vf or Vg is also provided,

Formula Ve
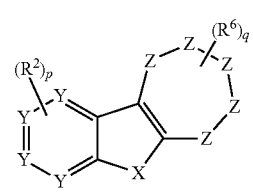

Formula Vf
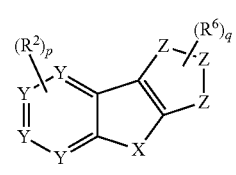

Formula Vg
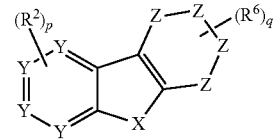

as are methods of using such a compound to stimulate the secretion and/or production of glucagon-like peptide-1 (GLP-1) and/or inhibit the activity of the Calcitonin Gene-Related Peptide (CGRP) receptor, and treat disease.

DETAILED DESCRIPTION OF THE INVENTION

It has now been found that certain metal salts and Brønsted acids effectively mediate regio- and diastereoselective three-component (4+3) cycloaddition reactions to furnish cyclohepta[b]indoles in high yields (Scheme 2). These reactions occur in a single step at room temperature without the need for Schlenk techniques, glove boxes, or inert atmosphere. Because each of the three coupling components (i.e., indole/furan/thiophene, aldehyde/ketone, coupling partner) can be independently varied, this methodology provides rapid access to a library of diverse cycloalkanyl[b]indole/benzofuran/benzothiophene derivatives.

SCHEME 2

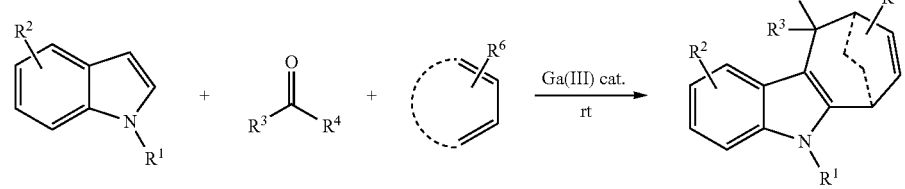

-continued

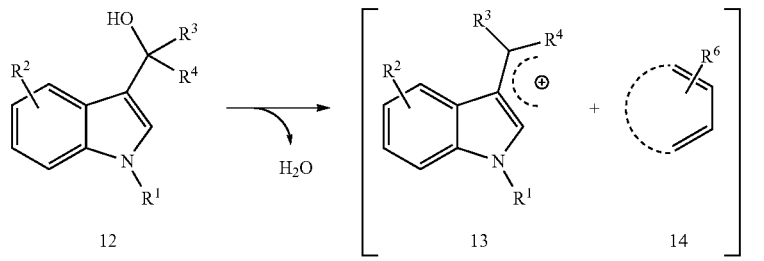

Given the data presented herein, this invention is a method for synthesizing cycloalkanyl[b]indoles, as well as related cycloalkanyl[b]benzofurans and cycloalkanyl[b]benzothiophenes, in acid-catalyzed three-component (4+3), (3+3) and (3+2) cycloaddition reactions. The method of the invention involves combining, in a single, multicomponent reaction, (1) an indole/furan/thiophene; (2) a ketone, or aldehyde or ketal; and (3) an appropriate coupling partner in the presence of an acid catalyst to produce a compound of Formula Va, Vb, Vc or Vd.

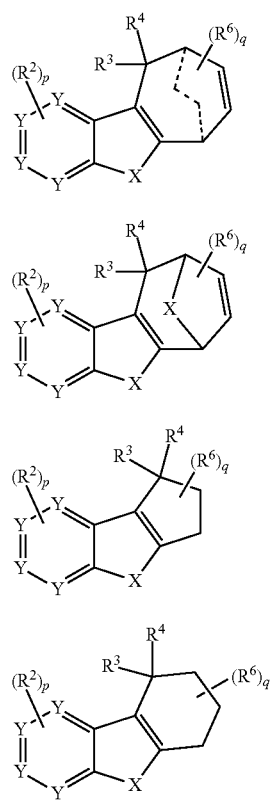

Formula Va

Formula Vb

Formula Vc

Formula Vd

More specifically, the method of the invention includes the steps of combining in a single reaction: (1) a compound of Formula I; (2) a ketone of Formula II, or an aldehyde or ketal of Formula III; and (3) a coupling partner in the presence of an acid catalyst to produce a compound of Formula Va, Vb, Vc or Vd.

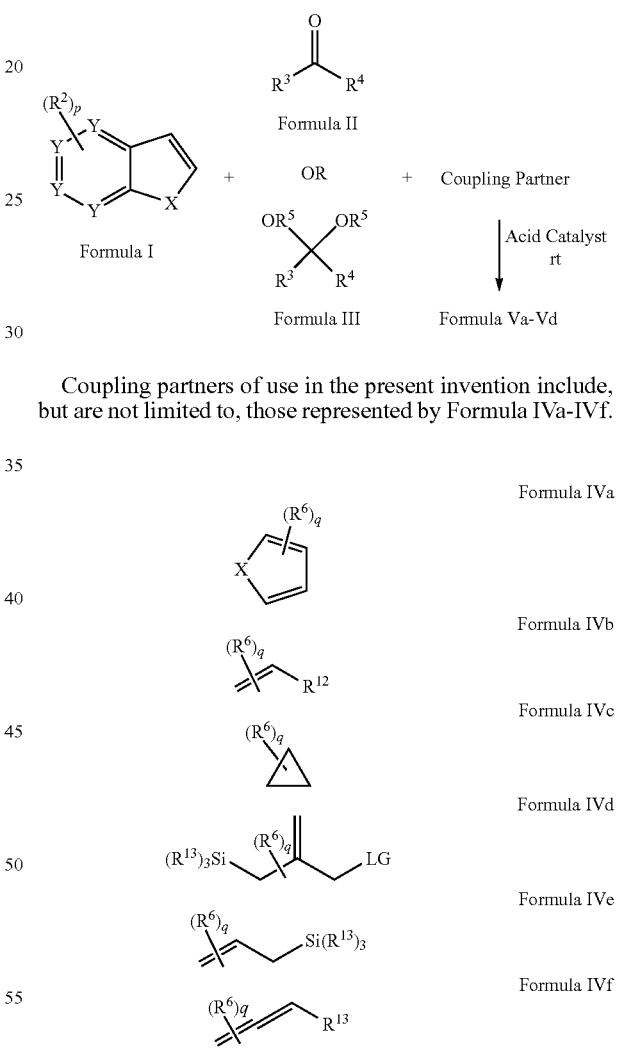

Coupling partners of use in the present invention include, but are not limited to, those represented by Formula IVa-IVf.

In reference to Formulae I-V, each X is the same or different and is independently $C-(R^1)_n$, $OR^1$, S or $NR^1$, wherein each $R^1$ is independently hydrogen, alkyl, alkenyl, alkynyl or aryl;

each Y is the same or different and is independently N or C;

each Z is the same or different and is independently N or C and wherein Z can optionally be connected to any other Z by a chain of one or more atoms independently selected from substituted or unsubstituted C, N, O, S, or a combination thereof, thereby forming an additional ring(s).

dashed bonds are independently present or absent such that this invention includes cyclopenta-, cyclohexa- and cyclohepta-compounds;

each $R^2$ is the same or different and is independently selected from the group of hydrogen, a halogen, haloalkyl, alkyl, alkoxy, alkenyl, alkynyl, cycloalkyl, cycloalkenyl, —$R^7$-cycloalkyl, aryl, —$NHR^7$, Het, —NHHet, —$NHR^7$Het, —$OR^8$, —O-aryl, —OHet, —$R^7OR^8$, —$NR^8R^9$, —$NR^8$-aryl, —$R^7NR^8R^9$, —$R^7NR^8$-aryl, —$R^7C(O)R^8$, —$C(O)R^8$, —$CO_2R^8$, —$R^7CO_2R^8$, —$C(O)NR^8R^9$, —$C(O)$aryl, —$C(O)NR^8$aryl, —$C(O)$Het, —$C(O)NHR^7$Het, —$R^7C(O)NR^8R^9$, —$C(S)NR^8R^9$, —$R^7C(S)NR^8R^9$, —$R^7(NH)NR^8R^9$, —$C(NH)NR^8R^9$, —$R^7C(NH)NR^8R^9$, —$S(O)_2NR^8R^9$, —$S(O)_2N R^8$aryl, —$R^7SO_2NHCOR^8$, —$R^7SO_2NR^8R^9$, —$R^7SO_2R^8$, —$S(O)_mR^8$, cyano, nitro, or azido group;

$R^3$ and $R^4$ are independently hydrogen, a halogen, haloalkyl, alkyl, alkoxy, alkenyl, alkynyl, cycloalkyl, cycloalkenyl, Het, aryl, —$NHR^7$, —NHHet, —$NHR^7$Het, —$OR^8$, —O-aryl, —OHet, —$R^7OR^8$, —$NR^8R^9$, —$NR^8$-aryl, —$R^7NR^8R^9$, —$R^7NR^8$-aryl, —$R^7C(O)R^8$, —$C(O)R^8$, —$CO_2R^8$, —$R^7CO_2R^8$, —$C(O)NR^8R^9$, —$C(O)$aryl, —$C(O)NR^8$aryl, —$C(O)$Het, —$C(O)NHR^7$Het, —$R^7C(O)NR^8R^9$, —$C(S)NR^8R^9$, —$R^7C(S)NR^8R^9$, —$R^7(NH)NR^8R^9$, —$C(NH)NR^8R^9$, —$R^7C(NH)NR^8R^9$, —$S(O)_2NR^8R^9$, —$S(O)_2N R^8$aryl, —$R^7SO_2NHCOR^8$, —$R^7SO_2NR^8R^9$, —$R^7SO_2R^8$, —$S(O)_mR^8$, cyano, nitro, or azido group, or $R^3$ and $R^4$ together form a $C_{4-6}$ cycoalkyl;

$R^5$ is hydrogen, a halogen, haloalkyl, alkyl, alkoxy, alkenyl, alkynyl, cycloalkyl, cycloalkenyl, Het or aryl group;

each $R^6$ is the same or different and is independently selected from the group of hydrogen, a halogen, haloalkyl, alkyl, alkoxy, alkenyl, alkynyl, cycloalkyl, cycloalkenyl, Het, aryl, —$NHR^7$, —NHHet, —$NHR^7$Het, —$OR^8$, —O-aryl, —OHet, —$R^7OR^8$, —$NR^8R^9$, —$NR^8$-aryl, —$R^7NR^8R^9$, —$R^7NR^8$-aryl, —$R^7C(O)R^8$, —$C(O)R^8$, —$CO_2R^8$, —$R^7CO_2R^8$, —$C(O)NR^8R^9$, —$C(O)$aryl, —$C(O)NR^8$aryl, —$C(O)$Het, —$C(O)NHR^7$Het, —$R^7C(O)NR^8R^9$, —$C(S)NR^8R^9$, —$R^7C(S)NR^8R^9$, —$R^7(NH)NR^8R^9$, —$C(NH)NR^8R^9$, —$R^7C(NH)NR^8R^9$, —$S(O)_2NR^8R^9$, —$S(O)_2N R^8$aryl, —$R^7SO_2NHCOR^8$, —$R^7SO_2NR^8R^9$, —$R^7SO_2R^8$, —$S(O)_mR^8$, cyano, nitro, or azido group;

each $R^7$ is the same or different and is independently selected from an alkylene, cycloalkylene, alkenylene, cycloalkenylene or alkynylene group;

each of $R^8$ and $R^9$ are the same or different and are independently selected from the group of hydrogen, alkyl, alkoxy, alkenyl, alkynyl, cycloalkyl, cycloalkenyl, —$R^7$cycloalkyl, —$R^7$OH, —$R^7(OR^7)_w$, or —$R^7NR^{10}R^{11}$ group;

each of $R^{10}$ and $R^{11}$ are the same or different and are independently selected from the group of an alkyl, cycloalkyl, alkenyl, cycloalkenyl, or alkynyl group;

each $R^{12}$ is independently is the same or different and is independently selected from the group of hydrogen, a halogen, haloalkyl, alkyl, alkoxy, alkenyl, alkynyl, cycloalkyl, cycloalkenyl, Het, aryl, —$NHR^7$, —NHHet, —$NHR^7$Het, —$OR^6$, —O-aryl, —OHet, —$R^7OR^8$, —$NR^8R^9$, —$NR^8$-aryl, —$R^7NR^8R^9$, —$R^7NR^8$-aryl, —$R^7C(O)R^8$, —$C(O)R^8$, —$CO_2R^8$, —$R^7CO_2R^8$, —$C(O)NR^8R^9$, —$C(O)$aryl, —$C(O)NR^8$aryl, —$C(O)$Het, —$C(O)NHR^7$Het, —$R^7C(O)NR^8R^9$, —$C(S)NR^8R^9$, —$R^7C(S)NR^8R^9$, —$R^7(NH)NR^8R^9$, —$C(NH)NR^8R^9$, —$R^7C(NH)NR^8R^9$, —$S(O)_2NR^8R^9$, —$S(O)_2N R^8$aryl, —$R^7SO_2NHCOR^8$, —$R^7SO_2NR^8R^9$, —$R^7SO_2R^8$, $R^9$, —$R^7SO_2R^8$, —$S(O)_mR^8$, cyano, nitro, or azido group;

each $R^{13}$ is independently C—$(R^1)_n$ or $OR^1$;

p is selected from 0, 1, 2, 3, or 4;

q is selected from 0, 1, 2, 3, or 4;

each n independently is 0, 1 or 2;

each m independently is 0, 1 or 2;

w is 1-10; and

LG is leaving group.

In some embodiments, at least two of the three dashed bonds in Formula Va are present. In other embodiments, all three dashed bonds in Formula Va are present.

Het represents an optionally substituted 5- or 6-membered heterocyclyl or heteroaryl group.

As used herein, the term "alkyl" refers to a straight or branched chain hydrocarbon, preferably having from one to twelve carbon atoms. Examples of "alkyl" as used herein include, but are not limited to, methyl, ethyl, propyl, isopropyl, isobutyl, n-butyl, tert-butyl, isopentyl, n-pentyl, and the like.

The term "alkenyl" refers to a straight or branched chain aliphatic hydrocarbon containing one or more carbon-to-carbon double bonds. Examples include, but are not limited to, vinyl, allyl, and the like.

As used herein, the term "alkynyl" refers to a straight or branched chain aliphatic hydrocarbon containing one or more carbon-to-carbon triple bonds. Examples include, but are not limited to, ethynyl and the like.

The term "alkylene" refers to a straight or branched chain divalent hydrocarbon radical, preferably having from one to ten carbon atoms. Alkylene groups as defined herein may optionally be substituted. Examples of "alkylene" as used herein include, but are not limited to, methylene, ethylene, n-propylene, n-butylene.

As used herein, the term "alkenylene" refers to a straight or branched chain divalent hydrocarbon radical, preferably having from one to ten carbon atoms, containing one or more carbon-to-carbon double bonds that may be optionally substituted. Examples include, but are not limited to, vinylene, allylene or 2-propenylene, and the like.

The term "alkynylene" refers to a straight or branched chain divalent hydrocarbon radical, preferably having from one to ten carbon atoms, containing one or more carbon-to-carbon triple bonds that may be optionally substituted. Examples include, but are not limited to, ethynylene and the like.

As used herein, the term "cycloalkyl" refers to an optionally substituted non-aromatic cyclic hydrocarbon ring, which optionally includes an alkylene linker through which the cycloalkyl may be attached. Exemplary "cycloalkyl" groups include, but are not limited to, cyclopropyl, cyclobutyl, cyclopentyl, cyclohexyl, cycloheptyl, and substituted versions thereof. As used herein, the term "cycloalkyl" includes an optionally substituted fused polycyclic hydrocarbon saturated ring and aromatic ring system, namely polycyclic hydrocarbons with less than maximum number of non-cumulative double bonds, for example where a saturated hydrocarbon ring (such as a cyclopentyl ring) is fused with an aromatic ring (herein "aryl," such as a benzene ring) to form, for example, groups such as indane.

As used herein, the term "cycloalkenyl" refers to an optionally substituted non-aromatic cyclic hydrocarbon ring containing one or more carbon-to-carbon double bonds which optionally includes an alkylene linker through which the cycloalkenyl may be attached. Exemplary "cycloalkenyl" groups include, but are not limited to, cyclopropenyl, cyclobutenyl, cyclopentenyl, cyclohexenyl, cycloheptenyl, and substituted versions thereof.

The term "cycloalkylene" refers to a divalent, optionally substituted non-aromatic cyclic hydrocarbon ring. Exemplary "cycloalkylene" groups include, but are not limited to, cyclopropylene, cyclobutylene, cyclopentylene, cyclohexylene, cycloheptylene, and the like.

As used herein, the term "cycloalkenylene" refers to a divalent optionally substituted non-aromatic cyclic hydrocarbon ring containing one or more carbon-to-carbon double bonds. Exemplary "cycloalkenylene" groups include, but are not limited to, cyclopropenylene, cyclobutenylene, cyclopentenylene, cyclohexenylene, cycloheptenylene, and the like.

As used herein, the term "heterocycle" or "heterocyclyl" refers to an optionally substituted mono- or polycyclic ring system containing one or more degrees of unsaturation and also containing one or more heteroatoms. Preferred heteroatoms include N, O, and/or S, including N-oxides, sulfur oxides, and dioxides. Preferably the ring is three to twelve-membered and is either fully saturated or has one or more degrees of unsaturation. Such rings may be optionally fused to one or more of another "heterocyclic" ring(s) or cycloalkyl ring(s). Examples of "heterocyclic" groups include, but are not limited to, tetrahydrofuran, pyran, 1,4-dioxane, 1,3-dioxane, piperidine, pyrrolidine, morpholine, tetrahydrothiopyran, and tetrahydrothiophene.

As used herein, the term "aryl" refers to an optionally substituted benzene ring or to an optionally substituted fused benzene ring system, for example anthracene, phenanthrene, or naphthalene ring systems. Examples of "aryl" groups include, but are not limited to, phenyl, 2-naphthyl, 1-naphthyl, and the like.

As used herein, the term "heteroaryl" refers to an optionally substituted monocyclic five to seven membered aromatic ring, or to an optionally substituted fused bicyclic aromatic ring system comprising two of such aromatic rings. These heteroaryl rings contain one or more nitrogen, sulfur, and/or oxygen atoms, where N-oxides, sulfur oxides, and dioxides are permissible heteroatom substitutions. Examples of "heteroaryl" groups used herein include, but should not be limited to, furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, benzofuran, benzothiophene, indole, indazole, benzimidizolyl, imidazopyridinyl, pyrazolopyridinyl, pyrazolopyrimidinyl, and the like.

As used herein, the term "halogen" refers to fluorine, chlorine, bromine, or iodine. In this respect, the term "haloalkyl" refers to an alkyl group, as defined herein, that is substituted with at least one halogen. Examples of branched or straight chained "haloalkyl" groups useful in the present invention include, but are not limited to, methyl, ethyl, propyl, isopropyl, n-butyl, and t-butyl substituted independently with one or more halogens, e.g., fluoro, chloro, bromo, and iodo. The term "haloalkyl" should be interpreted to include such substituents as perfluoroalkyl groups and the like.

As used herein, the term "alkoxy" refers to the group —O-alkyl. The term "nitro" refers to the group —$NO_2$. The term "cyano" refers to the group —CN. The term "azido" refers to the group —$N_3$. The term "acyl" refers to the group $R^a C(O)$—, where $R^a$ is alkyl, aryl, heteroaryl, or heterocyclyl, as each is defined herein.

As used herein throughout the specification, the phrase "optionally substituted" or variations thereof denote an optional substitution, including multiple degrees of substitution, with one or more substituent group. The phrase should not be interpreted so as to be imprecise or duplicative of substitution patterns herein described or depicted specifically. Rather, those of ordinary skill in the art will appreciate that the phrase is included to provide for obvious modifications, which are encompassed within the scope of the appended claims.

Exemplary optional substituent groups include acyl; alkyl; alkenyl; alkynyl; alkylsulfonyl; alkoxy; alkoxycarbonyl; cyano; halogen; haloalkyl; hydroxy; nitro; aryl, which may be further substituted with acyl, alkoxy, alkyl, alkenyl, alkynyl, alkylsulfonyl, cyano, halogen, haloalkyl, hydroxy, or nitro; heteroaryl, which may be further substituted with acyl, alkoxy, alkyl, alkenyl, alkynyl, alkylsulfonyl, cyano, halogen, haloalkyl, hydroxy, or nitro; arylsulfonyl, which may be further substituted with acyl, alkoxy, alkyl, alkenyl, alkynyl, alkylsulfonyl, cyano, halogen, haloalkyl, hydroxy, or nitro; heteroarylsulfonyl, which may be further substituted with acyl, alkoxy, alkyl, alkenyl, alkynyl, alkylsulfonyl, cyano, halogen, haloalkyl, hydroxy, or nitro; aryloxy, which may be further substituted with acyl, alkoxy, alkyl, alkenyl, alkynyl, alkylsulfonyl, cyano, halogen, haloalkyl, hydroxy, or nitro; heteroaryloxy, which may be further substituted with acyl, alkoxy, alkyl, alkenyl, alkynyl, alkylsulfonyl, cyano, halogen, haloalkyl, hydroxy, or nitro; or aryloxycarbonyl, which may be further substituted with acyl, alkoxy, alkyl, alkenyl, alkynyl, alkylsulfonyl, cyano, halogen, haloalkyl, hydroxy, or nitro.

According to the instant method, the multicomponent reaction is carried out in the presence of an acid catalyst. In some embodiments, the acid is a Lewis acid, e.g., a chiral Lewis acid complex. In some embodiments, the reaction is carried out at room temperature. In other embodiments, the reaction is carried out at 0 to 100° C. In still other embodiments, the acid is a Brønsted acid. To provide enantioselective variants of compounds of Formula V, other embodiments of the invention include the use of a chiral phosphoric acid or other chiral Brønsted acid.

Lewis acids include, but are not limited to, metal cations of aluminum(III), gallium(III), ferric(III), indium(III), antimony(V), tin(IV), titanium(IV), zinc(II), boron(III), and copper(II); and electron-deficient molecules such as boron trifluoride and aluminium trichloride. In some embodiments, the Lewis acid is a metal halide. Examples of metal halides include, but are not limited to, $AlBr_3$, $AlCl_3$, $GaBr_3$, $GaCl_3$, $FeCl_3$, $InI_3$, $InBr_3$, $InCl_3$, $SbCl_5$, $SnCl_4$, $TiCl_4$, $ZnCl_2$, $BF_3$, $BCl_3$ and lanthanide halides. In other embodiments, the Lewis acid is a metal salt. Examples of metal salts include, but are not limited to, triflates such as $Ga(OTf)_3$, $In(OTf)_3$, $Sc(OTf)_3$, $Ln(OTf)_3$ or $Cu(OTf)_2$. In particular embodiments the Lewis acid is a metal halide or triflate salt of Ga(III) or In(III).

Brønsted acids of use in the method of this invention include, but are not limited to, TFA, TfOH, AcOH, TsOH, $Tf_2NH$, MsOH and the like.

Chiral phosphoric acids of this invention have the structure of Formula VIa or VIb, or a racemic mixture thereof,

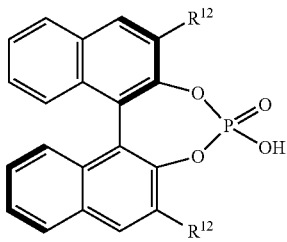

Formula VIa

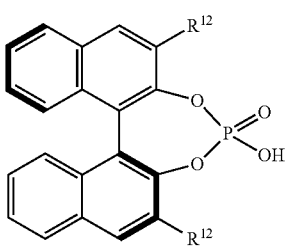

Formula VIb wherein,

R$^{12}$ is selected from groups including, but not limited to, a hydrogen, p-biphenyl, anthryl, SiPh$_3$, 3,5-bis(trifluoromethyl)phenyl, 2,4,6-triisopropylphenyl and NO$_2$C$_6$H$_5$. Such chiral phosphoric acid catalysts are known and available from commercial sources such as Sigma-Aldrich (St. Louis, Mo.) and include, but are not limited to (R)-(−)-1,1'-Binaphthyl-2,2'-diyl hydrogenphosphate, (S)-(+)-1,1'-Binaphthyl-2,2'-diyl hydrogenphosphate, (R)-(−)-3,3'-Bis(triphenylsilyl)-1,1'-binaphthyl-2,2'-diyl hydrogenphosphate, (S)-(+)-3,3'-Bis(triphenylsilyl)-1,1'-binaphthyl-2,2'-diyl hydrogenphosphate, (R)-3,3'-Bis[3,5-bis(trifluoromethyl)phenyl]-1,1'-binaphthyl-2,2'-diyl hydrogenphosphate, (R)-3,3'-Bis[3,5-bis(trifluoromethyl)phenyl]-1,1'-binaphthyl-2,2'-diyl hydrogenphosphate, (R)-3,3'-Bis(2,4,6-triisopropylphenyl)-1,1'-binaphthyl-2,2'-diyl hydrogenphosphate, (S)-3,3'-Bis(2,4,6-triisopropylphenyl)-1,1'-binaphthyl-2,2'-diyl hydrogenphosphate, and (R)-3,3'-Bis(9-anthracenyl)-1,1'-binaphthyl-2,2'-diyl hydrogenphosphate. See also, Cheon & Yamamoto (2008) *J. Am. Chem. Soc.* 130:9246-7.

Compounds of the invention may be provided as mixtures of stereoisomers as well as purified enantiomers or enantiomerically/diastereomerically enriched mixtures. Also included within the scope of the invention are the individual isomers of the compounds represented by Formula Va, Vb, Vc and Vd as well as any wholly or partially equilibrated mixtures thereof. Moreover, the instant compounds may be provided as pharmaceutically acceptable salts or solvates thereof.

Compounds produced by the method of this invention have been shown to stimulate the secretion and/or production of GLP-1 and/or inhibit the activity of the CGRP receptor. Therefore, the compounds of this invention can be provided in pharmaceutical compositions and used in methods for stimulating the secretion and/or production of GLP-1 and/or inhibiting the activity of the CGRP receptor.

In particular embodiments, a compound of use in the compositions and method of the invention has the structure of Formula Ve, Vf or Vg:

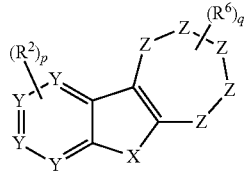

Formula Ve

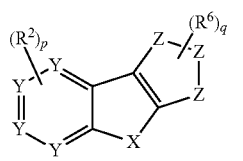

Formula Vf

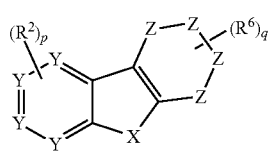

Formula Vg wherein X is C—(R$^1$)$_n$, OR$^1$, S or NR$^1$, wherein each R$^1$ is independently hydrogen, alkyl, alkenyl, alkynyl or aryl;

each Y is the same or different and is independently N or C;

each Z is the same or different and is independently N or C and wherein Z can optionally be connected to any other Z by a chain of one or more atoms independently selected from substituted or unsubstituted C, N, O, S, or a combination thereof, thereby forming an additional ring(s).

each R$^2$ is the same or different and is independently selected from the group of hydrogen, a halogen, haloalkyl, alkyl, alkoxy, alkenyl, alkynyl, cycloalkyl, cycloalkenyl, —R$^7$-cycloalkyl, aryl, —NHR$^7$, Het, —NHHet, —NHR$^7$Het, —OR$^8$, —O-aryl, —OHet, —R$^7$OR$^8$, —NR$^8$R$^9$, —NR$^B$-aryl, —R$^7$NR$^8$R$^9$, —R$^7$NR$^8$-aryl, —R$^7$C(O)R$^8$, —C(O)R$^8$, —CO$_2$R$^8$, —R$^7$CO$_2$R$^8$, —C(O)NR$^8$R$^9$, —C(O)aryl, —C(O)NR$^8$aryl, —C(O)Het, —C(O)NHR$^7$Het, —R$^7$C(O)NR$^8$R$^9$, —C(S)NR$^8$R$^9$, —R$^7$C(S)NR$^8$R$^9$, —R$^7$(NH)NR$^8$R$^9$, —C(NH)NR$^8$R$^9$, —R$^7$C(NH)NR$^8$R$^9$, —S(O)$_2$NR$^8$R$^9$, —S(O)$_2$N R$^8$aryl, —R$^7$SO$_2$NHCOR$^8$, —R$^7$SO$_2$NR$^8$R$^9$, —R$^7$SO$_2$R$^8$, —S(O)$_m$R$^8$, cyano, nitro, or azido group;

each R$^6$ is the same or different and is independently selected from the group of hydrogen, a halogen, haloalkyl, alkyl, alkoxy, alkenyl, alkynyl, cycloalkyl, cycloalkenyl, Het, aryl, —NHR$^7$, Het, —NHHet, —NHR$^7$Het, —OR$^8$, —O-aryl, —OHet, —R$^7$OR$^8$, —NR$^8$R$^9$, —NR$^B$-aryl, —R$^7$NR$^8$R$^9$, —R$^7$NR$^8$-aryl, —R$^7$C(O)R$^8$, —C(O)R$^8$, —CO$_2$R$^8$, —R$^7$CO$_2$R$^8$, —C(O)NR$^8$R$^9$, —C(O)aryl, —C(O)NR$^8$aryl, —C(O)Het, —C(O)NHR$^7$Het, —R$^7$C(O)NR$^8$R$^9$, —C(S)NR$^8$R$^9$, —R$^7$C(S)NR$^8$R$^9$, —R$^7$(NH)NR$^8$R$^9$, —C(NH)NR$^8$R$^9$, —R$^7$C(NH)NR$^8$R$^9$, —S(O)$_2$NR$^8$R$^9$, —S(O)$_2$N R$^8$aryl, —R$^7$SO$_2$NHCOR$^8$, —R$^7$SO$_2$NR$^8$R$^9$, —R$^7$SO$_2$R$^8$, —S(O)$_m$R$^8$, cyano, nitro, or azido group;

each R$^7$ is the same or different and is independently selected from an alkylene, cycloalkylene, alkenylene, cycloalkenylene or alkynylene group;

each of R$^8$ and R$^9$ are the same or different and are independently selected from the group of hydrogen, alkyl, alkoxy, alkenyl, alkynyl, cycloalkyl, cycloalkenyl, —R$^7$cycloalkyl, —R$^7$OH, —R$^7$(OR$^7$)$_w$, or —R$^7$NR$^{10}$R$^{11}$ group;

each of $R^{10}$ and $R^{11}$ are the same or different and are independently selected from the group of an alkyl, cycloalkyl, alkenyl, cycloalkenyl, or alkynyl group;

p is selected from 0, 1, 2, 3, or 4;

q is selected from 0, 1, 2, 3, or 4;

each n independently is 0, 1 or 2;

each m independently is 0, 1 or 2; and w is 1-10.

Any one of the compounds of this invention can be prepared as a salt, solvate or physiologically functional derivative. Typically, but not absolutely, the salts of the compounds of this invention are pharmaceutically acceptable salts. Salts encompassed within the term "pharmaceutically acceptable salts" refer to non-toxic salts of the compounds of this invention. Salts of the compounds of the invention may include acid addition salts. Representative salts include acetate, benzenesulfonate, benzoate, bicarbonate, bisulfate, bitartrate, borate, calcium edetate, camsylate, carbonate, clavulanate, citrate, dihydrochloride, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, laurate, malate, maleate, mandelate, mesylate, methylsulfate, monopotassium maleate, mucate, napsylate, nitrate, N-methylglucamine, oxalate, pamoate (embonate), palmitate, pantothenate, phosphate/diphosphate, polygalacturonate, potassium, salicylate, sodium, stearate, subacetate, succinate, sulfate, tannate, tartrate, teoclate, tosylate, triethiodide, trimethylammonium, and valerate salts. Other salts, which are not pharmaceutically acceptable, may be useful in the preparation of compounds of this invention and these should be considered to form a further aspect of the invention.

As used herein, the term "solvate" refers to a complex of variable stoichiometry formed by a solute (in this invention, a compound of Formula Va-Vg, or a salt or physiologically functional derivative thereof) and a solvent. Such solvents, for the purpose of the invention, should not interfere with the biological activity of the solute. Non-limiting examples of suitable solvents include, but are not limited to water, methanol, ethanol, and acetic acid. Preferably the solvent used is a pharmaceutically acceptable solvent. Non-limiting examples of suitable pharmaceutically acceptable solvents include water, ethanol, and acetic acid. Most preferably the solvent used is water.

As used herein, the term "physiologically functional derivative" refers to any pharmaceutically acceptable derivative of a compound of this invention that, upon administration to a mammal, is capable of providing (directly or indirectly) a compound of the invention or an active metabolite thereof. Such derivatives, for example, esters and amides, will be clear to those skilled in the art, without undue experimentation. Reference may be made to the teaching of Burger's Medicinal Chemistry and Drug Discovery, $5^{th}$ Edition, Vol 1: Principles and Practice.

Pharmaceutical compositions can be prepared by methods and contain carriers which are well-known in the art. A generally recognized compendium of such methods and ingredients is Remington: The Science and Practice of Pharmacy, Alfonso R. Gennaro, editor, 20th ed. Lippincott Williams & Wilkins: Philadelphia, Pa., 2000. A pharmaceutically acceptable carrier or vehicle, such as a liquid or solid filler, diluent, excipient, or solvent encapsulating material, is involved in carrying or transporting the subject agent from one organ, or portion of the body, to another organ, or portion of the body. Each carrier must be acceptable in the sense of being compatible with the other ingredients of the formulation and not injurious to the patient.

Examples of materials which can serve as pharmaceutically acceptable carriers include sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

When used in vivo, i.e., administered directly to a subject, the compounds of this invention can be administered by a variety of methods, e.g., orally, by injection (e.g. subcutaneous, intravenous, intraperitoneal, etc.), topically including via inhalation, transdermally, intranasally, intravaginally, or rectally according to standard medical practices.

Depending on the route of administration, the active compounds may be coated in a material to protect the compound from the action of acids and other natural conditions which may inactivate the compound. They may also be administered by continuous perfusion/infusion into a subject or provided as a prodrug.

To administer the therapeutic compound by other than parenteral administration, it may be necessary to coat the compound with, or co-administer the compound with, a material to prevent its inactivation. For example, the therapeutic compound may be administered to a patient in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan, et al. (1984) *J. Neuroimmunol.* 7:27).

The therapeutic compound may also be administered parenterally, intraperitoneally, intraspinally, or intracerebrally. Dispersions can be prepared in glycerol, liquid polyethylene glycols, and mixtures thereof and in oils. Under ordinary conditions of storage and use, these preparations may contain a preservative to prevent the growth of microorganisms.

Sterile injectable solutions can be prepared by incorporating a compound of the invention in the required amount in an appropriate solvent with one or a combination of ingredients enumerated above, as required, followed by filtered sterilization. Generally, dispersions are prepared by incorporating a compound of the invention into a sterile pharmaceutically acceptable carrier which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

A compound of the invention can be orally administered, for example, with an inert diluent or an assimilable edible carrier. The active agent and other ingredients may also be enclosed in a hard or soft shell gelatin capsule, compressed into tablets, or incorporated directly into the patient's diet. For oral therapeutic administration, the active agent may be incorporated with excipients and used in the form of ingestible tablets, buccal tablets, troches, capsules, elixirs, suspensions, syrups, wafers, and the like. The percentage of the active ingredient in the compositions and preparations may, of course, be varied. The amount of the active ingredient in such therapeutically useful compositions is such that a suitable dosage will be obtained.

It is especially advantageous to formulate parenteral compositions in dosage unit form for ease of administration and uniformity of dosage. Dosage unit form as used herein refers to physically discrete units suited as unitary dosages for the patients to be treated; each unit containing a predetermined quantity of active ingredient calculated to produce the desired therapeutic effect in association with the required pharmaceutical carrier. The specification for the dosage unit forms of the invention are dictated by and directly dependent on (a) the unique characteristics of the compound and the particular therapeutic effect to be achieved, and (b) the limitations inherent in the art of compounding an active ingredient for the treatment of a selected condition in a patient.

Active compounds are administered at a therapeutically effective dosage sufficient to treat a condition associated with a given patient. For example, the efficacy of a compound of this invention can be evaluated in an animal model system that may be predictive of efficacy in treating the disease in humans.

The actual dosage amount of a compound of the present disclosure or composition comprising a compound of the present disclosure administered to a patient may be determined by physical and physiological factors such as age, sex, body weight, severity of condition, the type of disease being treated, previous or concurrent therapeutic interventions, idiopathy of the patient and on the route of administration. These factors may be determined by a skilled artisan. The practitioner responsible for administration will typically determine the concentration of active ingredient(s) in a composition and appropriate dose(s) for the individual patient. The dosage may be adjusted by the individual physician in the event of any complication.

An effective amount typically will vary from about 0.001 mg/kg to about 1000 mg/kg, from about 0.01 mg/kg to about 750 mg/kg, from about 100 mg/kg to about 500 mg/kg, from about 1.0 mg/kg to about 250 mg/kg, from about 10.0 mg/kg to about 150 mg/kg in one or more dose administrations daily, for one or several days (depending of course of the mode of administration and the factors discussed above). Other suitable dose ranges include 1 mg to 10000 mg per day, 100 mg to 10000 mg per day, 500 mg to 10000 mg per day, and 500 mg to 1000 mg per day. In some particular embodiments, the amount is less than 10,000 mg per day with a range of 750 mg to 9000 mg per day.

The effective amount may be less than 1 mg/kg/day, less than 500 mg/kg/day, less than 250 mg/kg/day, less than 100 mg/kg/day, less than 50 mg/kg/day, less than 25 mg/kg/day or less than 10 mg/kg/day. It may alternatively be in the range of 1 mg/kg/day to 200 mg/kg/day. In other non-limiting examples, a dose may also comprise from about 1 micro-gram/kg/body weight, about 5 microgram/kg/body weight, about microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

Single or multiple doses of a compound described herein are contemplated. Desired time intervals for delivery of multiple doses can be determined by one of ordinary skill in the art employing no more than routine experimentation. As an example, patients may be administered two doses daily at approximately 12 hour intervals. In some embodiments, the compound is administered once a day.

The compound may be administered on a routine schedule. As used herein, a routine schedule refers to a predetermined designated period of time. The routine schedule may encompass periods of time which are identical or which differ in length, as long as the schedule is predetermined. For instance, the routine schedule may involve administration twice a day, every day, every two days, every three days, every four days, every five days, every six days, a weekly basis, a monthly basis or any set number of days or weeks there-between. Alternatively, the predetermined routine schedule may involve administration on a twice daily basis for the first week, followed by a daily basis for several months, etc. In other embodiments, the invention provides that the compound may taken orally and that the timing of which is or is not dependent upon food intake.

Glucagon-like peptide 1 (GLP-1) is secreted by the intestinal L-cells and is a potent antihyperglycemic hormone. GLP-1 functions by inducing glucose-dependent stimulation of insulin secretion and at the same time suppressing glucagon secretion. It has been reported that GLP-1 can also restore the glucose sensitivity of pancreatic β-cells. As a result, GLP-1 secretagogues are potential therapeutic agents for type diabetes. GLP-1 is also known to inhibit both gastric secretion and gastric emptying, thereby contributing to the feeling of satiety. Having demonstrated the stimulation of GLP-1 secretion and/or production, the compounds of this invention can also be used in the preparation of a dietary supplement, a food or feed product, or a beverage product for helping to sustain energy, helping control appetite, helping control blood sugar levels, reducing the risks associated with metabolic syndrome, reducing the risk associated with obesity and diabetes, reducing the risk associated with diabetes, helping to maintain healthy glucose and fat metabolism, or for helping to normalize production and release of GLP1 necessary for healthy glucose and fat metabolism, in a subject during and/or between meals or feedings comprising said dietary supplement, a food or feed product, or a beverage product.

In this respect, the invention also provides a method for stimulating GLP-1 secretion and/or production for helping to sustain energy, helping control appetite, helping control blood sugar levels, reducing the risks associated with metabolic syndrome, reducing the risk associated with obesity and diabetes, reducing the risk associated with diabetes, helping to maintain healthy glucose and fat metabolism, or for helping to normalize production and release of GLP-1 necessary for healthy glucose and fat metabolism, said method comprising administering to a subject an effective amount of a compound of the invention during and/or between meals or feedings. In some embodiments, a compound of the invention may provide a general improvement to human health and can protect against the harmful health effects associated with metabolic syndrome. It is also contemplated that a compound of the invention can protect against the harmful health effects associated with type 2 diabetes, and against the harmful health effects associated with obesity. The effect on GLP-1 secretion and/or production may be confirmed in an in vivo experiment such as described in Examples 5 and 6.

Furthermore, having demonstrated CGRP receptor inhibitory activity, the invention also provides methods for inhibiting CGRP receptor activity and in the treatment of pathophysiologic conditions where excessive CGRP receptor activation has occurred. Some of these include neurogenic vasodilation, neurogenic inflammation, migraine, cluster headache and other headaches, thermal injury, circulatory shock, menopausal flushing, and asthma. CGRP receptor activation has been implicated in the pathogenesis of migraine headache (Edvinsson (2001) *CNS Drugs* 15(10): 745-53; Williamson (2001) *Microsc. Res. Tech.* 53:167-178; Grant (2002) Brit. *J. Pharmacol.* 135:356-362). Serum levels of CGRP are elevated during migraine (Goadsby, et al. (1990) *Ann. Neurol.* 28:183-7) and treatment with anti-migraine drugs returns CGRP levels to normal coincident with alleviation of headache (Gallai, et al. (1995) *Cephalalgia* 15:384-90). Migraineurs exhibit elevated basal CGRP levels compared to controls (Ashina, et al. (2000) *Pain* 86(1-2):133-8). Intravenous CGRP infusion produces lasting headache in migraineurs (Lassen, et al. (2002) *Cephalalgia* 22(1):54-61). Preclinical studies in dog and rat report that systemic CGRP blockade with the peptide antagonist CGRP(8-37) does not alter resting systemic hemodynamics nor regional blood flow (Shen, et al. (2001) *J. Pharmacol. Exp. Ther.* 298:551-8). Thus, CGRP-receptor antagonists may present a novel treatment for migraine that avoids the cardiovascular liabilities of active vasoconstriction associated with non-selective 5-HT1B/1D agonists.

The invention is described in greater detail by the following non-limiting examples.

Example 1

Lewis Acid and Brønsted Acid Catalyzed Synthesis of Cyclohepta[b]Indoles

It has been shown that treatment of 2-furfuryl alcohols with stoichiometric TiCl$_4$ promotes the formation of furfuryl cations for (4+3) cycloaddition reactions (Winne, et al. (2011) *Angew. Chem. Int. Ed.* 50:11900; Pattenden & Winne (2009) *Tetrahedron Lett.* 50:7310). Therefore, it was speculated that nucleophilic addition of indole at C3 to either an aldehyde or ketone would furnish alcohol 12 (Scheme 2). In the presence of an appropriate Lewis acid, water would be ejected to generate the requisite allylic cation 13 for (4+3) cycloaddition reactions. Ga(III)-catalyzed processes have been described (Lauer, et al. (2011) *J. Am. Chem. Soc.* 133:9119; Han & Wu (2010) *Org. Lett.* 12:5780; Robertson & Wu (2010) *Org. Lett.* 12:2668) and therefore these Lewis acids were used in the title reaction. Ga(III) salts, and in particular Ga(OTf)$_3$ (Olah, et al. (1988) *J. Am. Chem. Soc.* 11:2560; Prakash, et al. (2007) *Proc. Natl. Acad. Sci. USA* 104:3703; Prakash, et al. (2007) *Org. Lett.* 9:179; Prakash, et al. (2003) *Catal. Lett.* 85:1; Yan, et al. (2005) *Catal. Lett.* 103:165) are stable to air and moisture and therefore ideal in the present case because an equivalent of water is formed in the reaction.

TABLE 1

| Entry[a] | Catalyst | Comments[d] |
|---|---|---|
| 1 | Ga(OTf)$_3$ | Full conversion, impurities hard to separate |
| 2 | GaBr$_3$ | Full conversion, clean reaction (85% yield) |
| 3[b] | GaBr$_3$ | Slow reaction |
| 4[c] | GaBr$_3$ | Only 12 observed |
| 5 | GaCl$_3$ | Mostly 12 observed |
| 6 | In(OTf)$_3$ | Substantial decomposition |
| 7 | InI$_3$ | Full conversion, clean reaction |
| 8 | InBr$_3$ | Slow reaction |
| 9 | InCl$_3$ | Mostly 12 observed |
| 10 | Sc(OTf)$_3$ | Slow reaction |
| 11 | Cu(OTf)$_2$ | Only 12 observed |
| 12 | TFA | Only 12 observed |
| 13 | TfOH | Full conversion, impurities hard to separate |

[a]10 mol % catalyst, 2 equiv. 9a, 5 equiv 10a, rt, CH$_2$Cl$_2$.
[b]Toluene for EtOAc as solvent.
[c]THF or Et$_2$O as solvent.
[d]Diastereoselectivities were 3:1 to 5:1 for all reactions in which product was observed (as determined by $^1$H NMR spectroscopy).

As is evident from Table 1, both Ga(OTf)$_3$ and GaBr$_3$ were effective in promoting the desired reaction. Ga(OTf)$_3$ was qualitatively the more reactive catalyst. But because it also generated a by-product (not formed with the use of GaBr$_3$) that was difficult to separate from 11a, the scope of the transformation was analyzed using GaBr$_3$. InI$_3$ was also effective but several other Lewis acids (entries 6-11) resulted in either slow reaction rates or varying amounts of alcohol 12.

The scope of the three-component (4+3) cycloaddition reaction was quite broad (Table 2). A variety of combinations involving indoles 8a-e, aldehydes 9a-e and 16, acetal 15, ketones 17a-c, and dienes 10a-e were surveyed. The reaction was tolerant to N-H indoles as well as alkylation at nitrogen. Aldehydes, ketones, and acetals were appropriate electrophilic components. Electron-withdrawing or -donating groups on either the indole or carbonyl components were compatible. Electron-rich substrates such as 8d, 9b, and 9d-e appeared to accelerate reaction rate. With less reactive substrates (11i, 11k-11n) the use of Ga(OTf)$_3$ was beneficial for achieving higher yields and shorter reaction times. The presence of halides in 11s-u offers a convenient handle for additional elaboration of the indole core through transitional metal-catalyzed cross-coupling reactions.

TABLE 2
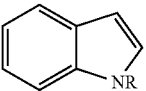
8a; R = Me
8b; R = Bn
8c; R = H
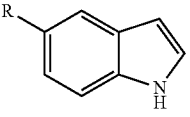
8d; R = MeO
8e; R = MeO$_2$C
8f-h; R = Cl, Br, I
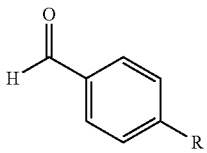
9a; R = H
9b; R = MeO
9c; R = CF$_3$
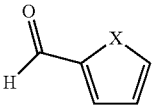
9d; X = O
9e; X = S
10a
10b
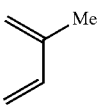
10c
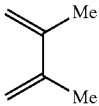
10d
TABLE 2-continued
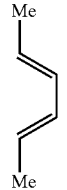
10e
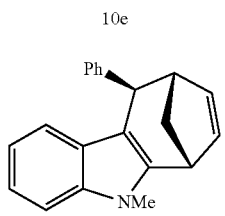
11a
(94%, 4:1 dr)$^a$
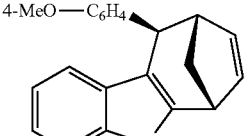
11b
(75%, 10:1 dr)$^a$
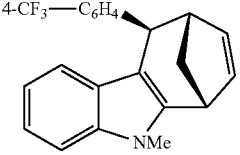
11c
(85%, 2:1 dr)$^a$
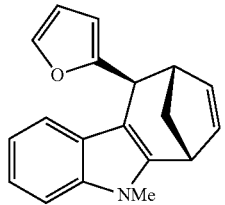 [SMILES: Cn1c2c(c3ccccc31)[C@@H](c1ccco1)[C@@H]1C=C[C@H]2C1]
(83, >10:1 dr)$^a$
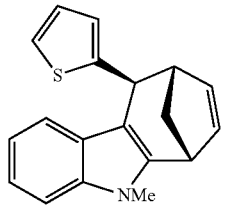 [SMILES: Cn1c2c(c3ccccc31)[C@@H](c1cccs1)[C@@H]1C=C[C@H]2C1]
11e
(83%, 10:1 dr)$^a$
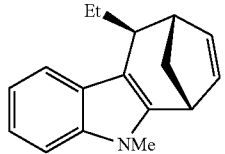 [SMILES: CC[C@@H]1c2c(n(C)c3ccccc23)[C@H]2C=C[C@@H]1C2]
11f
(82% 1:1 dr)$^a$ TABLE 2-continued 11g (94%)[a]

11h (84%)[a]

11i (81%)[b]

11j (91%)[e,f]

11k (59%)[b]

11l (46%)[c] (17%)[d]

11m (48%)[c] (21%)[d]

11n (54%, >10:1 dr)[c,e] (29%)[d]

11o (86%)[a]

11p; R = H (87%)[e,f]
11q; R = OMe (76%)[a]
11r; R = CO₂Me (76%)[a]
11s; R = Cl (75%)[a]
11t; R = Br (73%)[a]
11u; R = I (82%)[a]

15

16

TABLE 2-continued

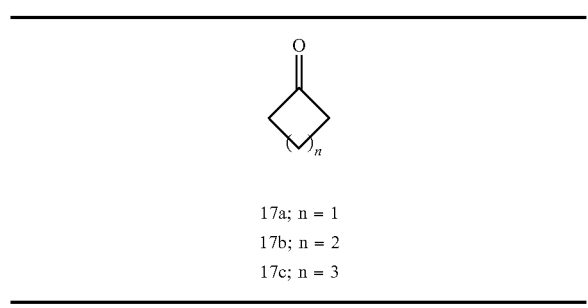

17a; n = 1
17b; n = 2
17c; n = 3

[a] indole (1 equiv), electrophile (2 equiv), diene (5 equiv), GaBr$_3$ (10 mol %), RT.
[b] indole (1 equiv), electrophile (2 equiv), diene (5 equiv), Ga(OTf)$_3$ (10 mole %), RT.
[c] indole (1 equiv), electrophile (1.1 equiv), diene (5 equiv), Ga(OTf)$_3$ (20 mole %), RT.
[d] Yield with 20% TfOH.
[e] Structure confirmed by single crystal X-ray analysis.
[f] 2 mmol scale, 5 mol % GaBr$_3$, all else same.

For products 11a-f, diastereoselectivities were observed in the range of >10:1 to 1:1. Electron-rich aldehydes appeared to couple with the highest selectivities while electron-poor and linear alkyl substrates furnished products with lower selectivities. When the use of the unsymmetrical diene, isoprene (10c), was examined, the desired product 11m was isolated as a single regioisomer. The structures of 11j, 11n and 11p were confirmed by single-crystal X-ray crystallography.

To gain insight into the mechanism of this reaction, density-functional-theory (DFT) calculations were performed using the M06 functional (Zhao & Truhlar (2008) *Acc. Chem. Res.* 41:157; Zhao & Truhlar (2003) *Theor. Chem. Acc.* 120:215) and the 6-311G**++ basis set (Krishnan, et al. (1980) *J. Chem. Phys.* 72:650; McLean & Chandler (1980) *J. Chem. Phys.* 72:5639; Clark, et al. (1983) *J. Comput. Chem.* 4:294; Frisch, et al. (1984) *J. Chem. Phys.* 80:3265) as implemented in the Jaguar program. For the reaction of cyclopentadiene (10a) with the indolyl cation derived from indole (8c) and ketal 15, the lowest energy pathway was identified as a two-step process. Rather than a concerted pericyclic reaction, an intermediate was formed by initial C—C bond formation between the terminal carbon of the indolyl cation and a terminal diene carbon, followed by closure of the 7-membered ring. Transition states for both steps were located, and an overall reaction free energy profile was generated. A stepwise mechanism was observed as proposed for related (4+3) reactions (Winne, et al. (2011) supra).

Example 2

Chiral Phosphoric Acid Catalyzed Synthesis of Cyclohepta[b]Indoles

An investigation to develop enantioselective variants of this transformation was also initiated. This analysis indicated that chiral phosphoric acid 18 catalyzed the reaction between indole (8c), anisaldehyde (9b), and (10) to furnish the desired product liv in 64% ee (eq 1) (Scheme 4).

SCHEME 4

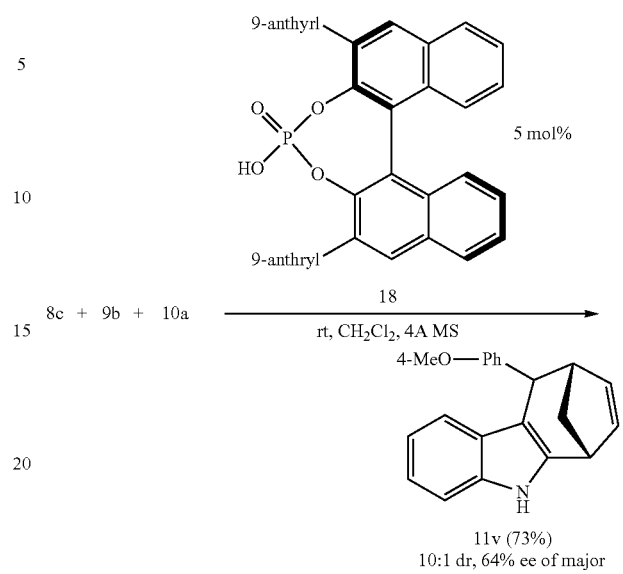

11v (73%)
10:1 dr, 64% ee of major

Several chiral Ga(III) and In(III) complexes are known (Li, et al. (2005) *Adv. Synth. Catal.* 347:1247; Li, et al. (2002) *Chem Commun.* 2994: Lv, et al. (2011) *Angew. Chem. Int. Ed.* 50:6612; Teo, et al. (2005) *Org. Lett.* 7:2743; Gutierrez, et al. (2011) *Org. Lett.* 13:5754) and have been utilized to promote transformations with excellent ee's. Therefore, these catalysts may also be of use in the synthesis of the title reaction.

Example 3

Lewis Acid and Brønsted Acid Catalyzed Synthesis of Cyclopenta[b]indoles

Cyclopenta[b]indoles were also synthesized using the method of this invention. Schemes 5 and 6 illustrate the synthesis of two exemplary cyclopenta[b]indoles prepared with TfOH.

SCHEME 5

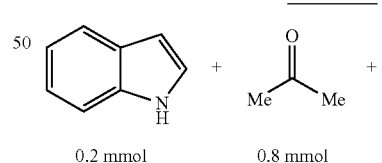

0.2 mmol    0.8 mmol

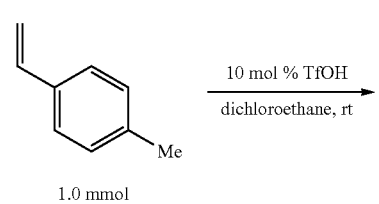

1.0 mmol

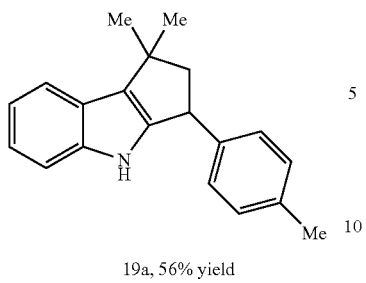
19a, 56% yield
SCHEME 6
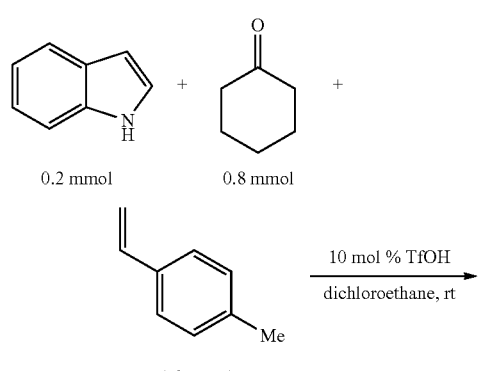
19b, 80% yield
Table 3 provides examples of additional compounds and their respective yields using TfOH.
TABLE 3
| Compound | Product | Yield with TfOH | Reaction Time |
|---|---|---|---|
| 19c | 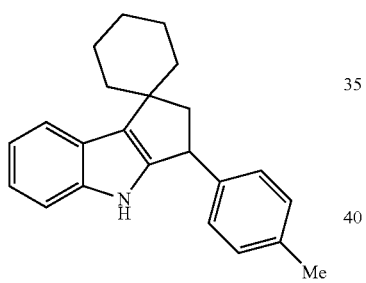 | 80% | 40 min. |
| 19d | | 62% | 1 hour |
| 19e | | 64% | 3 hours |
| 19f | | 64% | 3 hours |
| 19g | | 83% | 15 min. |
| 19h | | 52% | 1 hour |

TABLE 3-continued

| Compound | Product | Yield with TfOH | Reaction Time |
|---|---|---|---|
| 19i | | 58% | 40 min. |
| 19j | | 50% | 2 hours |

Reaction conditions: 1 equiv indole, 4 equiv ketone, 5 equiv alkene, 0.5 equiv TfOH, room temperature in dichloroethane as solvent.

In similar reactions using Bi(OTf)$_3$, additional cyclopenta[b]indoles were synthesized (Table 4).

TABLE 4

| Compound | Structure | Yield with Bi(OTf)$_3$ |
|---|---|---|
| 19k[a] | | 51% |
| 19l[d] | | 46% |
| 19m[c] | 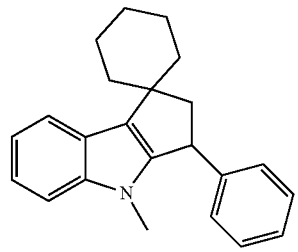 [SMILES: Cn1c2c(c3ccccc31)C1(CCCCC1)CC2c1ccccc1] | 51% |
| 19n[b] | 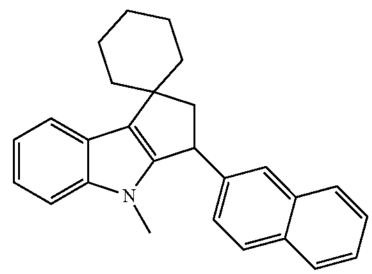 [SMILES: Cn1c2c(c3ccccc31)C1(CCCCC1)CC2c1ccc2ccccc2c1] | 13% |
| 19o[c] | 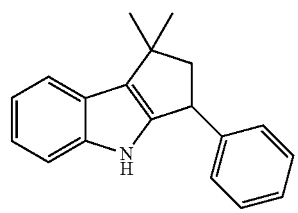 [SMILES: CC1(C)CC(c2ccccc2)c2[nH]c3ccccc3c21] | 41% |
| 19p[c] | 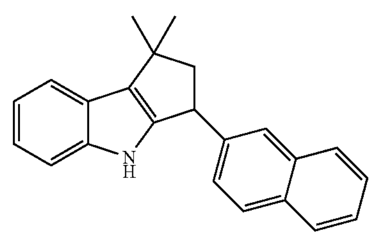 [SMILES: CC1(C)CC(c2ccc3ccccc3c2)c2[nH]c3ccccc3c21] | 25% |
| 19q[c] | 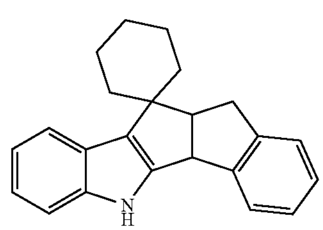 [SMILES: c1ccc2c(c1)CC1C2c2[nH]c3ccccc3c2C12CCCCC2] | 32% |

[a]10% catalyst used;
[b]15% catalyst used;
[c]20% catalyst used, 40° C.

Scheme 7 illustrates the synthesis of another exemplary cyclopenta[b]indole prepared with Ga(OTf)$_3$.

SCHEME 7

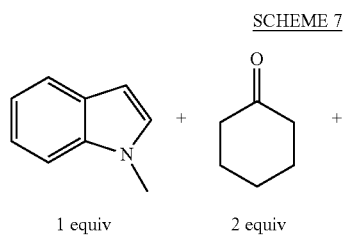

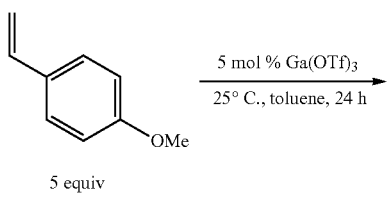

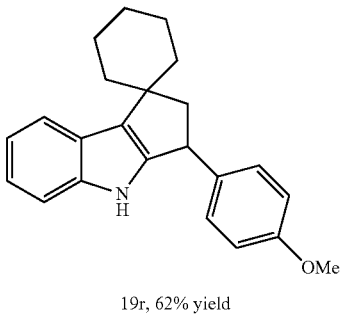

19r, 62% yield

The use of In(OTf)₃ in the preparation of cyclopenta[b] indoles was also demonstrated (Table 5).

TABLE 5

| Compound | Product | Yield with In(OTf)₃ |
|---|---|---|
| 19s | (structure) | 64% |
| 19t[a] | (structure) | 65% |

[a]10% Catalyst, 40° C.

Example 4

In Vitro Activity

Selected compounds of this invention were screened for K-Ras Wnt synthetic lethal, anti-angiogenic activity, Wnt pathway modulatory activity, insulin and GLP-1 secretion modulatory activity, GPR119 receptor agonist activity, mGlu2R antagonist activity, CGRP receptor antagonist activity, Apelin receptor agonist activity and hexokinase 2 inhibitory activity using the PD$^2$ and TD$^2$ Screening Panel (Eli Lilly & Company). See Lee, et al. (2011) *J. Biomol. Screen.* 16:588-602. The results of this analysis are presented in Table 6.

TABLE 6

| | | Compound | |
|---|---|---|---|
| Activity | Assay | 11s | 11t |
| K-Ras Wnt | HCT116 KrasSL % Inhibit | | |
| | @ 0.2 μM | 2.3% | 5.3% |
| | @ 2 μM | −38% | −11.5% |
| | @ 20 μM | 96.4% | 103.9% |
| | RKO KrasSL % Inhibit | | |
| | @ 0.2 μM | −2.8%* | −5.8%* |
| | @ 2 μM | 14.4%* | 17.6%* |
| | @ 20 μM | 101.7%* | 102.2%* |
| | Colo320 KrasSL % Inhibit | | |
| | @ 0.2 μM | 33.3% | −6.6% |
| | @ 2 μM | 15.8 | 23.1% |
| | @ 20 μM | 150.3% | 151.5% |

TABLE 6-continued

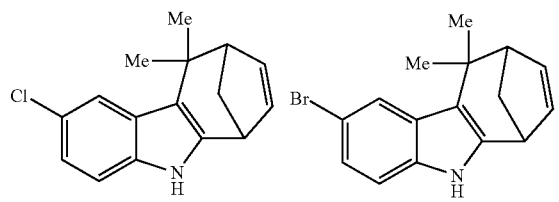

| Activity | Assay | 11s | 11t |
|---|---|---|---|
| | SNU-C1 KrasSL | | |
| | % Inhibit | | |
| | @ 0.2 μM | 15.7% | −1% |
| | @ 2 μM | 5.5% | −19.1% |
| | @ 20 μM | 106.4% | 107.2% |
| Anti-Angiogenic | Angio Tube Area | | |
| | % Inhibit | | |
| | @ 2 μM | 21.7% | 8% |
| | @ 10 μM | 21.8% | 38% |
| Wnt Pathway | Osteo bCat | | |
| | % Stimulation | | |
| | @ 2 μM | 1.3% | 1.8% |
| | @ 10 μM | 9.3% | 5.5% |
| Insulin | Secretion Hi Gluc | | |
| Secretion | % Stimulation | | |
| | @ 2 μM | −1.2% | 0.1% |
| | @ 10 μM | 15.8% | 19.1% |
| GLP-1 | hNCI GLP-1 | | |
| Secretion | Secretion | | |
| | % Stimulation | | |
| | @ 2 μM | −1.7% | 0% |
| | @ 20 μM | 108% | 35.2% |
| | $EC_{50}$ (μM) | 34.828 | 29.052 |
| GPR 119 | hGPR119 | | |
| Receptor Agonist | agonism | | |
| | % Stimulation | | |
| | @ 10 μM | −5.1% | −2.3% |
| mGlu2R | hMGLUR2 | | |
| Antagonist | % Inhibition | | |
| | @ 50 μM | −20.4% | −19.7% |
| CGRP Receptor | hCGRP1 | | |
| Antagonist | Antagonism | | |
| | % Inhibition | | |
| | @ 30 μM | 77.1% | 67.7% |
| | $IC_{50}$ (nM) | 0 | 0 |
| Apelin Receptor | hApelin | | |
| Agonist | agonism | | |
| | % Stimulation | | |
| | @ 30 μM | −46.2% | −52.8% |
| Hexokinase 2 | hHK2 ADP-FP | | |
| Inhibitor | % Inhibition | | |
| | @ 20 μM | 5.5% | 3.2% |

*Average of three independent experiments.

^ Average of three independent experiments.

This analysis indicated that compounds 11s and 11t exhibited both stimulatory activity for the secretion and/or production of GLP-1, and inhibitory activity for the CGRP receptor with $EC_{50}$ values of 35 and 29 μM, respectively.

In light of the above results, additional compounds (Table 7) were prepared and phenotypic assays were carried out using hNCI-H716 and mSTC-1 cell lines to monitor GLP-1 secretion (single point (SP) and concentration response curves (CRC)) (Table 8), as well as a secondary assay with pituitary cells (Table 9).

TABLE 7

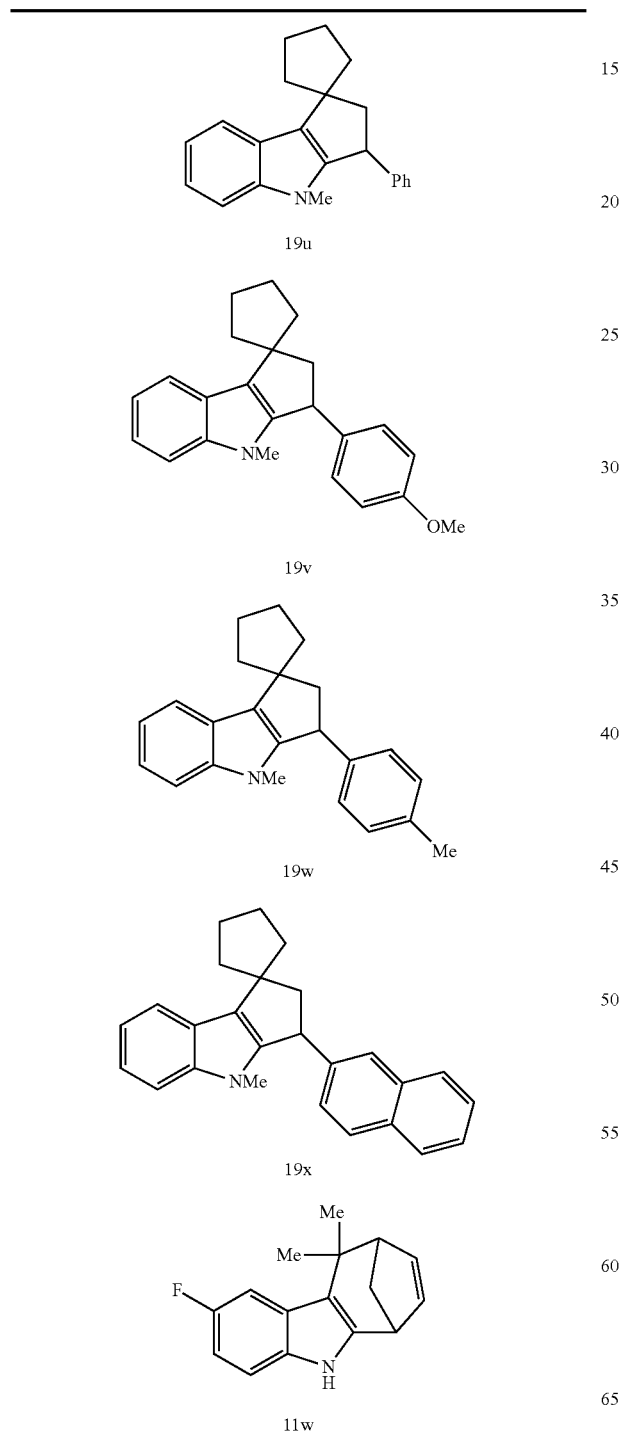

TABLE 7-continued

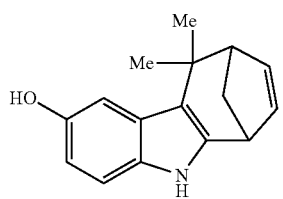 [SMILES: CC1(C)c2c([nH]c3ccc(O)cc23)C2C=CC1C2]

11x

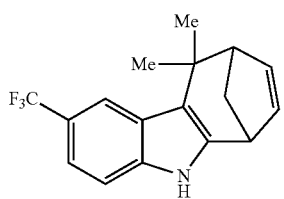 [SMILES: CC1(C)c2c([nH]c3ccc(C(F)(F)F)cc23)C2C=CC1C2]

11y

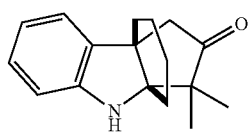

20

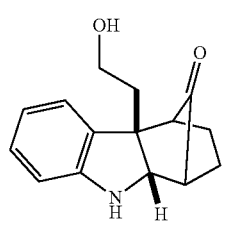 [SMILES: O=C1C2CCC1[C@@]1(CCO)c3ccccc3N[C@@H]21]

21

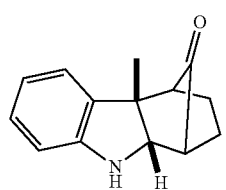 [SMILES: C[C@]12c3ccccc3N[C@H]1C1CCC2C1=O]

22

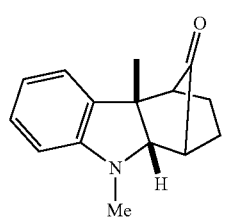 [SMILES: CN1c2ccccc2[C@]2(C)C3CCC(C3=O)[C@H]12]

23

TABLE 7-continued
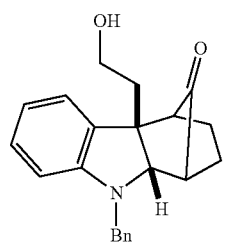 [SMILES: O=C1C2CCC1[C@@]1(CCO)c3ccccc3N(Cc3ccccc3)[C@@H]21]
24
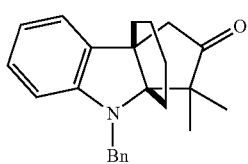 [SMILES: CC1(C)C(=O)C[C@]23CCCC[C@]12N(Cc1ccccc1)c1ccccc13]
25
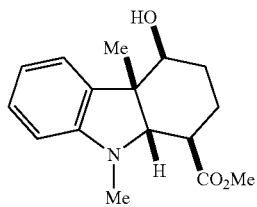 [SMILES: COC(=O)[C@@H]1CC[C@H](O)[C@@]2(C)c3ccccc3N(C)[C@@H]12]
26
TABLE 7-continued
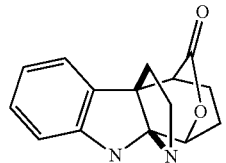
27
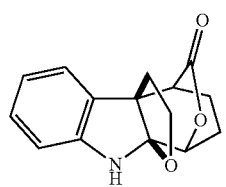 [SMILES: O=C1OC2CCC1[C@]13CCO[C@]21Nc1ccccc13]
28
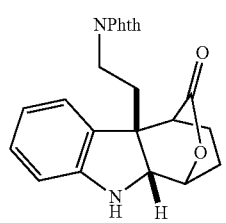
29
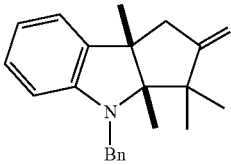
30
TABLE 8
| Compound | Primary SP | | | | Primary CRC (EC$_{50}$, μM) | | | |
|---|---|---|---|---|---|---|---|---|
| | hNCI (% Stim.) | | mSTC (% Stim.) | | | | | |
| | 2 μM | 20 μM | 2 μM | 20 μM | mSTC | hNCI | mSTC LDH | hNCI Basal |
| 11a | −2.8 | −0.5 | | | | | | |
| 11b | −0.5 | −2.4 | | | | | | |
| 11c | 1 | 0.7 | | | | | | |
| 11d | −2.5 | −1 | | | | | | |
| 11e | −0.5 | −2.4 | | | | | | |
| 11f | −1.1 | −2.4 | | | | | | |
| 11g | −0.8 | −2.7 | | | | | | |
| 11h | −2.2 | −3.3 | | | | | | |
| 11i | 0 | −6 | | | | | | |
| 11j | −0.3 | −3.3 | | | | | | |
| 11k | 3.1 | −1.9 | | | | | | |
| 11l | −2 | −3.3 | | | | | | |
| 11m | −2.2 | −1 | | | | | | |
| 11n | 10.3 | −3.5 | | | | | | |
| 11o | −0.3 | −2.1 | | | | | | |
| 11p | −0.5 | 23.3 | | | | | | |
| 11q | 1.3 | 5.9 | | | | | | |
| 11r | −1.1 | 13.4 | | | | | | |

TABLE 8-continued

| | Primary SP | | | | Primary CRC (EC$_{50}$, μM) | | mSTC LDH | hNCI Basal |
|---|---|---|---|---|---|---|---|---|
| | hNCI (% Stim.) | | mSTC (% Stim.) | | | | | |
| Compound | 2 μM | 20 μM | 2 μM | 20 μM | mSTC | hNCI | | |
| 11u | 0 | 57 | | | 2.0 | >40.0 | | 35.77 |
| | | | | | 3.2 | 14.7 | | |
| | | | | | | 24.5 | | |
| | | | | | | 26.7 | | |
| 11t | 0 | 35.2 | | | 2.4 | 29.1 | | |
| | | | | | 4.1 | 17.6 | | |
| | | | | | 2.2 | 16.4 | | |
| 11s | −1.7 | 108 | | | 1.9 | 34.8 | | >40.0 |
| | | | | | 3.6 | 33.5 | | |
| | | | | | 5.0 | 23.2 | | |
| | | | | | | >40.0 | | |
| 19u | −0.8 | −3.8 | | | | | | |
| 19v | −2 | −2.4 | | | | | | |
| 19w | −0.8 | −1.9 | | | | | | |
| 19x | −3.1 | −3.3 | | | | | | |
| 11w | 1.4 | 41.3 | | | 23.55 | 22.39 | | |
| | | | | | 22.75 | 30.27 | | |
| 11x | 3.4 | −0.8 | | | >40.0 | >40.0 | | |
| 11y | −0.4 | 55.9 | | | 10.4 | 35.57 | | |
| | | | | | 5.88 | 17.02 | | |
| 19h | 0 | 0 | 93.2 | 107 | | | | |
| 19b | 24 | 0 | 17.6 | 124.8 | >40.0 | >40.0 | | |
| 19e | 0 | 0 | 78.4 | 109.1 | | | | |
| 19i | 0 | 23.4 | 13.5 | 103.6 | >40.0 | >40.0 | | |
| 19g | 0 | 0 | 34.9 | 123.8 | | | | |
| 19d | 0 | 0 | 10.3 | 53.6 | | | | |
| 20 | −0.2 | −1.1 | −4.1 | 8.2 | | | | |
| 21 | 4.3 | 3.4 | −1 | −2.4 | | | | |
| 22 | −1.5 | −1.3 | −1.8 | 7.4 | | | | |
| 23 | 6.4 | −1.1 | 6.9 | 71.3 | 6.18 | >40.0 | >40.0 | >40.0 |
| | | | | | | | >40.0 | |
| 24 | 1 | 4.6 | −3.3 | 47.9 | 15.21 | >40.0 | >40.0 | >40.0 |
| | | | | | 13.45 | | >40.0 | |
| 25 | 0.6 | −1.1 | 78.5 | 51.1 | 0.20 | >40.0 | >40.0 | >40.0 |
| | | | | | | | >40.0 | |
| 26 | 1.4 | −1.3 | −2.4 | −3.1 | | | | |
| 27 | 1 | 0.4 | −5.1 | −3.9 | | | | |
| 28 | 1.2 | 4 | −2.4 | 4.4 | | | | |
| 29 | 6 | 0.2 | −0.2 | 49.5 | >40.0 | >40.0 | >40.0 | >40.0 |
| | | | | | 10.97 | | >40.0 | |
| 30 | 3.1 | −0.2 | 49.9 | 49.9 | 0.85 | >40.0 | >40.0 | >40.0 |
| | | | | | 0.51 | | >40.0 | | hNCI, hNCI-H716; mSTC, mSTC-1; LDH, LDH Secretion. Basal, Basal LDH secretion.

TABLE 9

| | Pituitary Cells (Growth Hormone Secretion, % Stimulation) | |
|---|---|---|
| Compound | @ 3.3 μM | @ 11 μM |
| 11u | 9.3 | 6.5 |
| | 14.5 | −15.2 |
| | 28.9 | −20.6 |
| 11t | −12.6 | 2.4 |
| | −7.1 | −8.1 |
| 11s | −10.0 | −22.6 |
| | −17.7 | −37.6 |
| | −18.6 | −14.6 |

Example 5

In Vivo Activity in Animal Model

Mice (male C57BL/6, 8-10 weeks of age) were fasted overnight by being placed in a clean cage without food. The next day, all mice were weighed and assigned to groups of similar body weights. Test compounds were formulated in 1% HEC, 0.25% TWEEN 80, 0.05% antifoam (vehicle control). Compounds 11s and 11u were orally dosed (100 mg/kg) and cardiac sticks were done on $CO_2$ euthanized mice at 30 minutes post-dose. Blood (500+μL whole blood) from the cardiac stick was placed in chilled EDTA-plasma tubes with inhibitors, DPP4 inhibitor (5 μL/500 μL blood) and aprotinin (bovine lung, 11 HL/500 μL blood), and stored on ice. Plasma was separated by centrifugation and aliquoted for compound exposure to total GIP and GLP-1 (X-36 amide). Plates for compound exposure were analyzed for absorption, distribution, metabolism, and excretion, while conventional kits were used for GLP-1 (x-36) amide (Mesoscale) and GIP (Millipore) analyses.

This analysis indicated that the lower limit of quantification (LLOQ) for Compounds 11s and 11u was 1.0 ng/mL and the upper limit of quantification (ULOQ) was 5000 ng/mL in plasma. The mean (±standard deviation) plasma levels and respective coefficient of variation (% CV) following oral administration of Compound 11s were 411.92±88.15 ng/ml and 21.4, respectively. Similarly, the mean plasma levels and respective % CV of Compound 11u were 201.6±37.24 ng/ml and 18.47, respectively. Plasma GLP-1 and GIP responses to oral Compounds 11s and 11u are presented in Table 10.

TABLE 10

| Treatment | Avg. GLP-1 (pg/mL) ±SEM | Avg. GIP (pg/mL) ±SEM |
|---|---|---|
| Vehicle (1% HEC) | 5.79 ± 0.61 | 25.16 ± 6.72 |
| Compound 11s | 5.52 ± 1.18 | 23.42 ± 7.44 |
| Compound 11u | 7.66 ± 0.89 | 26.23 ± 10.35 |

Example 6

In Vivo Activity in Human Subjects

Healthy volunteers that have fasted for 10 hours are given enteral feeding by a duodenal tube. Each volunteer is given two different liquid meals (bolus, 55-65 ml) on four different days (A-D),
Day A: Test Compound in 50 ml glycerol+5 ml ethanol
Day B: oleic acid (1.54 g) in 50 ml glycerol+5 ml ethanol (=control Day A)
Day C: Test Compound (2 g)+glucose (10-20g in 10 ml water) in 50 ml glycerol+5 ml ethanol
Day D: oleic acid (1.54 g)+glucose (10-20g in 10 ml water) in 50 ml glycerol+5 ml ethanol (=control Day C)

Blood samples are collected at −15, −10, 0, 10, 20, 30, 40, 50, 60, 75, 90, 120, 150, 180, and 240 minutes. In addition, a 1 mL sample is collected from the duodenal lumen at 15 and 30 minutes. Insulin and C-peptide levels are measured in the serum; glucose, GLP-1, glucose-dependent insulinotrophic polypeptide (GIP), glucagon, peptide-YY, and cholecystokinin are measured in plasma; and bilirubin levels in duodenal samples are measured. The methods for these assays are known in the art. See, e.g., Hojberg, et al. (2008) *Diabet. Med.* 25:1268-1275. GLP-1 secretion and/or production is expected to be stimulated in subjects receiving a compound described herein.

What is claimed is:

1. A method for synthesizing a cycloalkanyl[b]indole, comprising
    (a) combining, in a single reaction,
        (i) a compound of Formula I,

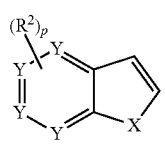

Formula I (ii) a compound of Formula II or III, and

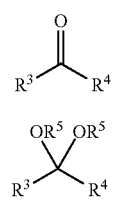

Formula II

Formula III (iii) a coupling partner; and (b) adding an acid catalyst thereby producing a compound of Formula Va, Vb, Vc or Vd

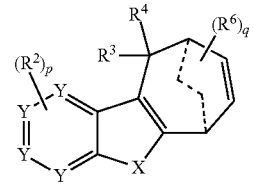

Formula Va

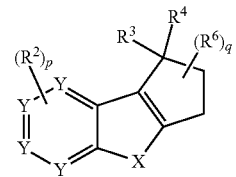

Formula Vc

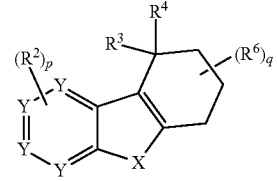

Formula Vd wherein,
X is $NR^1$, wherein $R^1$ is hydrogen, or alkyl
each Y is C;
at least two of the three dashed bonds are present;
each $R^2$ is the same or different and is independently selected from the group of hydrogen, a halogen, alkyl, alkoxy, aryl, $-NHR^7$, $-OR^8$, $-O$-aryl, $-NR^8R^9$, $-NR^8$-aryl, $-C(O)R^8$, $-CO_2R^8$, $-C(O)NR^8R^9$, $-C(O)$aryl, $-C(O)NR^8$aryl, $-C(O)$ Het, $-C(O)$ $NHR^7$Het, $-S(O)_2NR^8R^9$, $-S(O)_2N$ $R^8$aryl, and cyano;
$R^3$ and $R^4$ are independently hydrogen, alkyl, cycloalkyl, aryl, $-NHR^7$, $-OR^8$, $-O$-aryl, $-NR^8R^9$, $-NR^8$-aryl, $-C(O)NR^8R^9$, $-C(O)$aryl, $-C(O)NR^8$aryl, $-C(O)$ Het, $-C(O)NHR^7$Het, $-S(O)_2NR^8R^9$, $-S(O)_2N$ $R^8$aryl, and cyano, or
$R^3$ and $R^4$ together form a $C_{4-6}$ cycoalkyl;
$R^5$ is alkyl;
each $R^6$ is the same or different and is independently selected from the group of hydrogen, alkyl, cycloalkyl, and aryl;
each $R^7$ is the same or different and is independently selected from an alkylene, cycloalkylene, alkenylene, cycloalkenylene or alkynylene group;
each of $R^8$ and $R^9$ are the same or different and are independently selected from the group of hydrogen, an alkyl, alkoxy, alkenyl, alkynyl, cycloalkyl, cycloalkenyl, $-R^7$cycloalkyl, $-R^7OH$, $-R^7(OR^7)_w$, or $-R^7NR^{10}R^{11}$ group;
each of $R^{10}$ and $R^{11}$ are the same or different and are independently selected from the group of an alkyl, cycloalkyl, alkenyl, cycloalkenyl, or alkynyl group;
p is selected from 0, 1, or 2;
q is selected from 0, 1, or 2;
w is 1-10.

2. The method of claim 1, wherein the acid catalyst is a Lewis acid, chiral Lewis acid complex, Brønsted acid, chiral phosphoric acid, or other chiral Brønsted acid.

3. The method of claim 2, wherein the Lewis acid comprises a metal halide or triflate salt of Ga(III) or In(III).

4. The method of claim 1, wherein the coupling partner is a compound having the structure of Formula IVa, IVb, IVc or IVe:

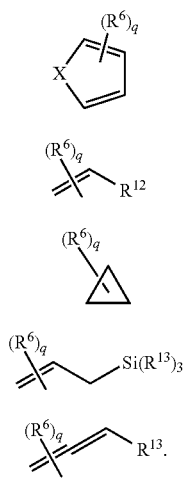

Formula IVa

Formula IVb

Formula IVc

Formula IVe

Formula IVf wherein X is C—$(R^1)_n$, wherein each $R^1$ is hydrogen;
$R^{12}$ is hydrogen; and
n is 1 or 2.

5. A compound having the structure of Formula Vc, or a pharmaceutically acceptable salt or solvate thereof:

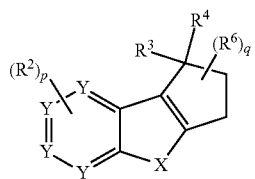

Formula Vc wherein,
X is $NR^1$, wherein $R^1$ is hydrogen, or alkyl
each Y is C;
each $R^2$ is the same or different and is independently selected from the group of hydrogen, a halogen, alkyl, alkoxy, aryl, —$NHR^7$, —$OR^8$, —O-aryl, —$NR^8R^9$, —$NR^8$-aryl, —$C(O)R^8$, —$CO_2R^8$, —$C(O)NR^8R^9$, —C(O)aryl, —$C(O)NR^8$aryl, —C(O)Het, —C(O)NHR$^7$Het, —$S(O)_2NR^8R^9$, —$S(O)_2N$ $R^8$aryl, and cyano;
$R^3$ and $R^4$ are independently selected from the group of alkyl, cycloalkyl, aryl, —$C(O)R^8$, —$CO_2R^8$, —$C(O)NR^8R^9$, —C(O)aryl, —$C(O)NR^8$aryl, —C(O)Het, —C(O)NHR$^7$Het, —$S(O)_2NR^8R^9$, —$S(O)_2N$ $R^8$aryl, and cyano, or
$R^3$ and $R^4$ together form a $C_{4-6}$ cycloalkyl;
each $R^6$ is the same or different and is independently selected from the group of alkyl, cycloalkyl, and aryl;
each $R^7$ is the same or different and is independently selected from an alkylene, cycloalkylene, alkenylene, cycloalkenylene or alkynylene group;
each of $R^8$ and $R^9$ are the same or different and are independently selected from the group of hydrogen, an alkyl, alkoxy, alkenyl, alkynyl, cycloalkyl, cycloalkenyl, —$R^7$cycloalkyl, —$R^7$OH, —$R^7(OR^7)_w$, or —$R^7NR^{10}R^{11}$ group;
each of $R^{10}$ and $R^{11}$ are the same or different and are independently selected from the group of an alkyl, cycloalkyl, alkenyl, cycloalkenyl, or alkynyl group;
p is selected from 0, 1, or 2;
q is selected from 0, 1, or 2; and
w is 1-10;
provided that when $R^1$ is alkyl, q is 1.

6. The compound of claim 5, wherin each $R^6$ is aryl.

7. The compound of claim 5, wherein $R^3$ and $R^4$ are independently alkyl.

8. The compound of claim 5, wherein $R^6$ is aryl, and $R^3$ and $R^4$ are independently alkyl.

9. The compound of claim 5, wherein $R^3$ and $R^4$ together form a $C_{4-6}$ cycloalkyl.

10. The compound of claim 5, wherein $R^6$ is aryl, and $R^3$ and $R^4$ together form a $C_{4-6}$ cycloalkyl.

11. The compound of claim 5, selected from the following, and pharmaceutically acceptable salts thereof:

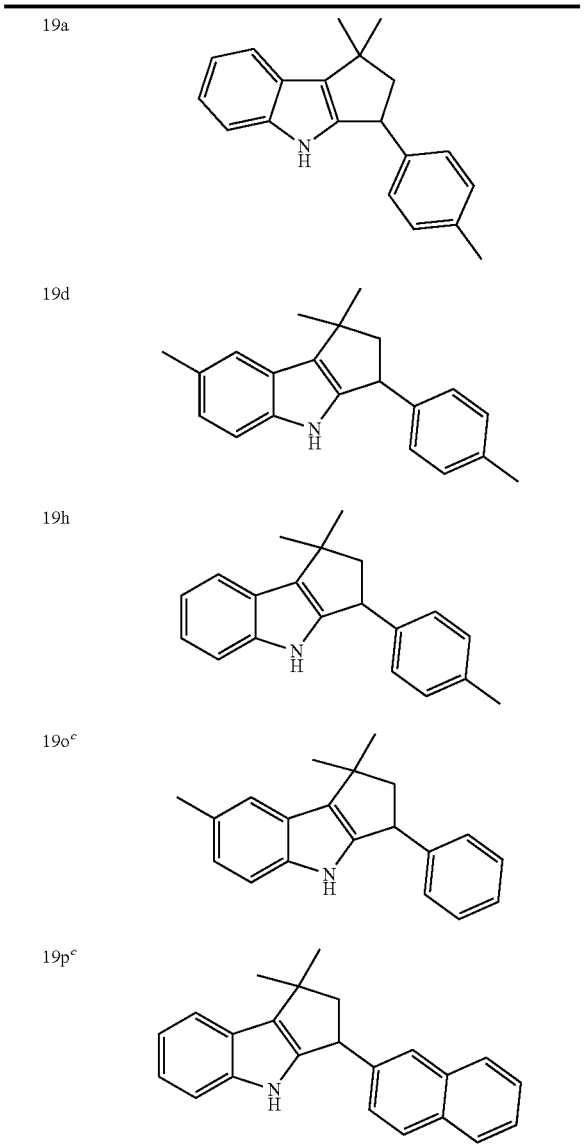

-continued
19s 
19c 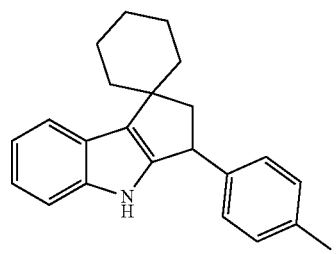 [SMILES: Cc1ccc(C2CC3(CCCCC3)c3c2[nH]c2ccccc32)cc1]
19e 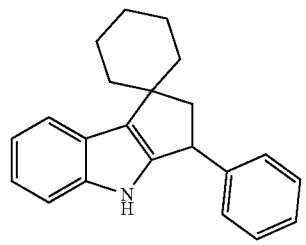 [SMILES: c1ccc(C2CC3(CCCCC3)c3c2[nH]c2ccccc32)cc1]
19f 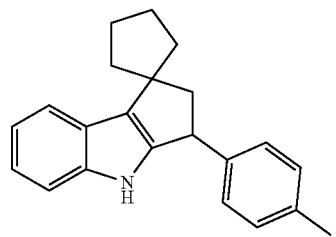 [SMILES: Cc1ccc(C2CC3(CCCC3)c3c2[nH]c2ccccc32)cc1]
19g 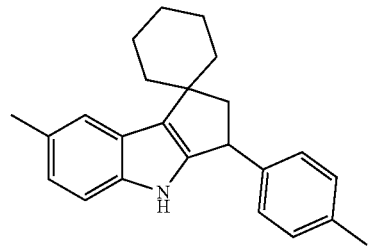
19i 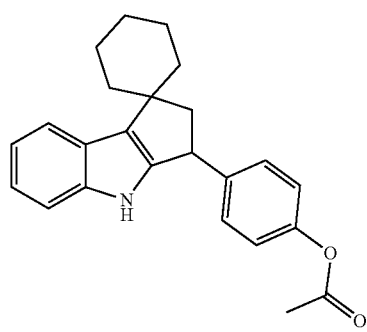 [SMILES: CC(=O)Oc1ccc(C2CC3(CCCCC3)c3c2[nH]c2ccccc32)cc1]
-continued
19j 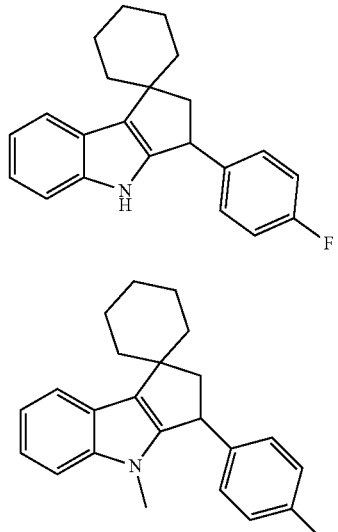
19l 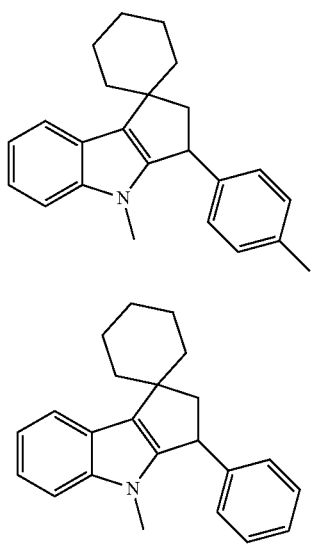
19m 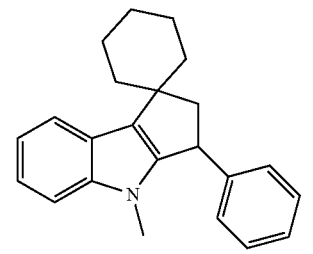 [SMILES: Cn1c2c(c3ccccc31)C1(CCCCC1)CC2c1ccccc1]
19n 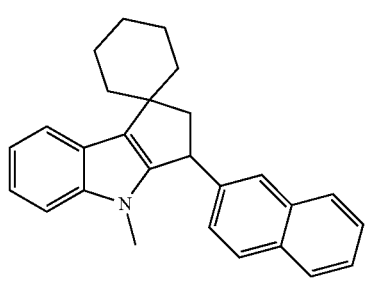 [SMILES: Cn1c2c(c3ccccc31)C1(CCCCC1)CC2c1ccc2ccccc2c1]
19r 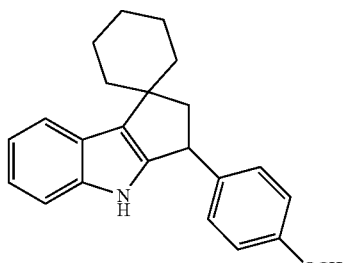
19t 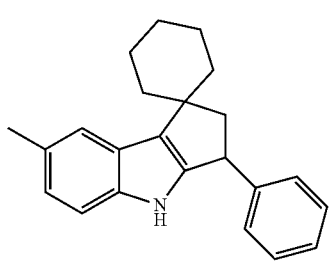 [SMILES: Cc1ccc2[nH]c3c(c2c1)C1(CCCCC1)CC3c1ccccc1]

-continued

19u
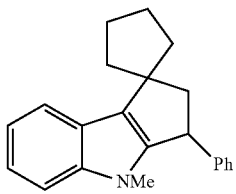 [SMILES: Cn1c2c(c3ccccc31)C1(CCCC1)CC2c1ccccc1]

19v
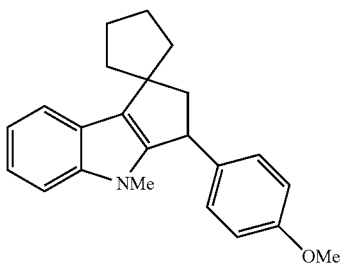 [SMILES: COc1ccc(C2CC3(CCCC3)c3c2n(C)c2ccccc32)cc1]

19w
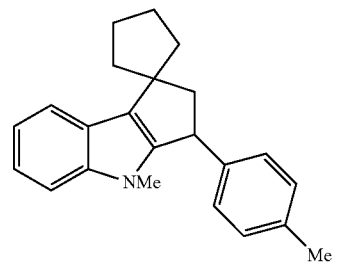 [SMILES: Cc1ccc(C2CC3(CCCC3)c3c2n(C)c2ccccc32)cc1]

19x
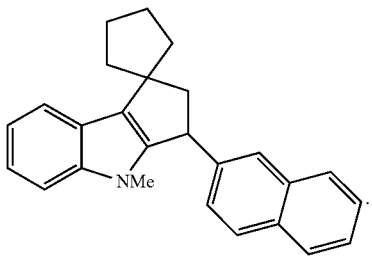 [SMILES: Cn1c2c(c3ccccc31)C1(CCCC1)CC2c1ccc2ccccc2c1]

12. A method for stimulating the secretion and/or production of glucagon-like peptide-1 (GLP-1) or inhibiting the activity of Calcitonin Gene-Related Peptide (CGRP) receptor comprising contacting a cell with a compound of claim 5 so that the secretion and/or production of GLP-1 is stimulated or the activity of the CGRP receptor is inhibited.

13. A compound having the structure of Formula Va, or a pharmaceutically acceptable salt or solvate thereof:

Formula Va
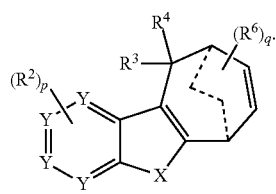

wherein
X is $NR^1$, wherein $R^1$ is hydrogen or alkyl;
each Y is C;
at least two of the three dashed bonds are present;
each $R^2$ is the same or different and is independently selected from the group of hydrogen, a halogen, alkyl, alkoxy, aryl, $-NHR^7$, $-OR^8$, $-O$-aryl, $-NR^8R^9$, $-NR^8$aryl, $-C(O)R^8$, $-CO_2R^8$, $-C(O)NR^8R^9$, $-C(O)$aryl, $-C(O)NR^8$aryl, $-C(O)$Het, $-C(O)NHR^7$Het, $-S(O)_2NR^8R^9$, $-S(O)_2N\ R^8$aryl, and cyano;

$R^3$ is hydrogen, cycloalkyl, Het, aryl, $-C(O)R^8$, $-CO_2R^8$, $-C(O)NR^8R^9$, $-C(O)$aryl, $-C(O)NR^8$aryl, $-C(O)$Het, $-C(O)NHR^7$Het, $-S(O)_2NR^8R^9$, $-S(O)_2N\ R^8$aryl, —and cyano; and $R^4$ is alkyl, cycloalkyl, Het, aryl, $-C(O)R^8$, $-CO_2R^8$, $-C(O)NR^8R^9$, $-C(O)$aryl, $-C(O)NR^8$aryl, $-C(O)$Het, $-C(O)NHR^7$Het, $-S(O)_2NR^8R^9$, $-S(O)_2N\ R^8$aryl, and cyano; or $R^3$ and $R^4$ together form a $C_{4-6}$ cycloalkyl;

each $R^6$ is the same or different and is independently selected from the group of alkyl, cycloalkyl, and aryl;

each $R^7$ is the same or different and is independently selected from an alkylene, cycloalkylene, alkenylene, cycloalkenylene or alkynylene group;

each of $R^8$ and $R^9$ are the same or different and are independently selected from the group of hydrogen, an alkyl, alkoxy, alkenyl, alkynyl, cycloalkyl, cycloalkenyl, $-R^7$cycloalkyl, $-R^7OH$, $-R^7(OR^7)_w$, or $R^7NR^{10}R^{11}$ group;

each of $R^{10}$ and $R^{11}$ are the same or different and are independently selected from the group of an alkyl, cycloalkyl, alkenyl, cycloalkenyl, or alkynyl group;

p is selected from 0, 1, or 2;
q is selected from 0, 1, or 2;
and
w is 1-10.

14. The compound of claim 13 having the structure:

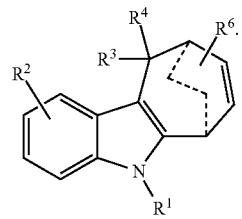

15. The compound of claim 14, wherein two of the three dashed bonds are present, forming a five-membered ring.

16. The compound of claim 13, wherein two of the three dashed bonds are present, and wherein the compound of Formula Va has the structure:

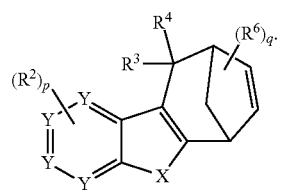

17. The compound of claim 13, wherein each $R^2$ is the same or different and is independently selected from the group of alkyl and aryl.

18. The compound of claim 13, wherein $R^3$ and $R^4$ together form a $C_{4-6}$ cycloalkyl.

19. The compound of claim 13, wherein R3 is selected from the group of hydrogen, alkyl, cycloalkyl, aryl, and Het and R4 is selected from the group of alkyl, cycloalkyl, aryl, and Het.

20. The compound of claim 13, selected from the following:
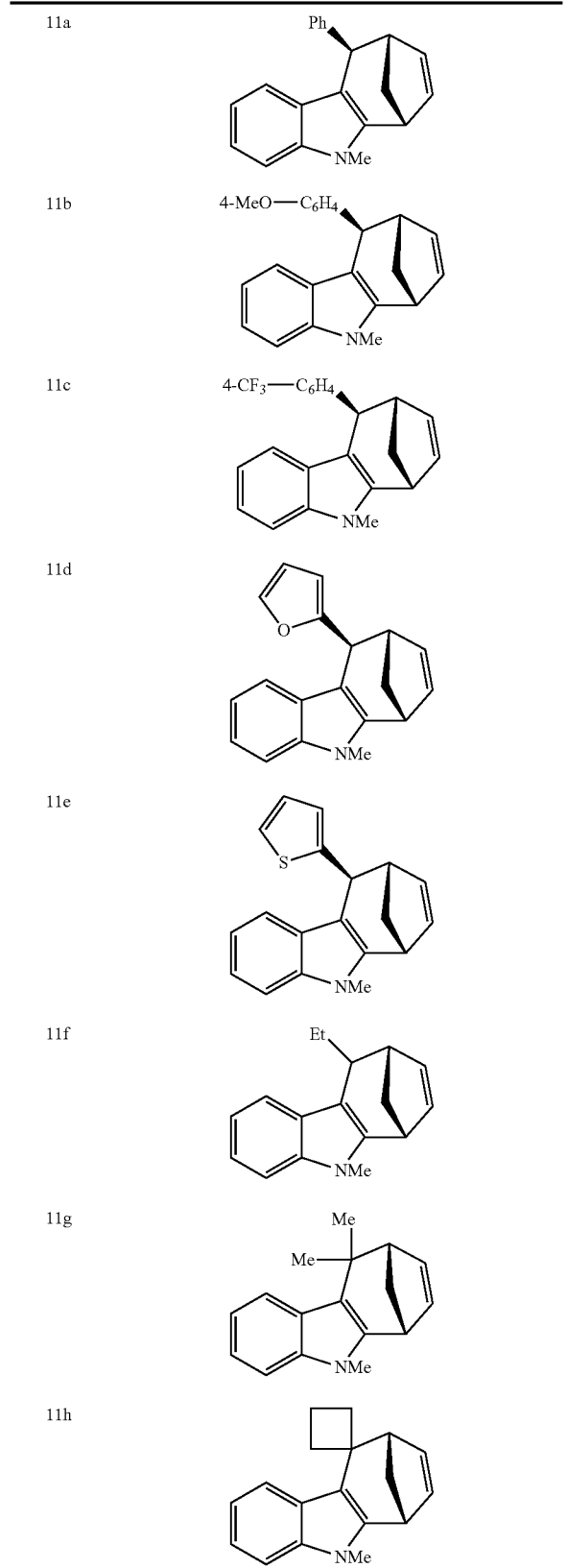
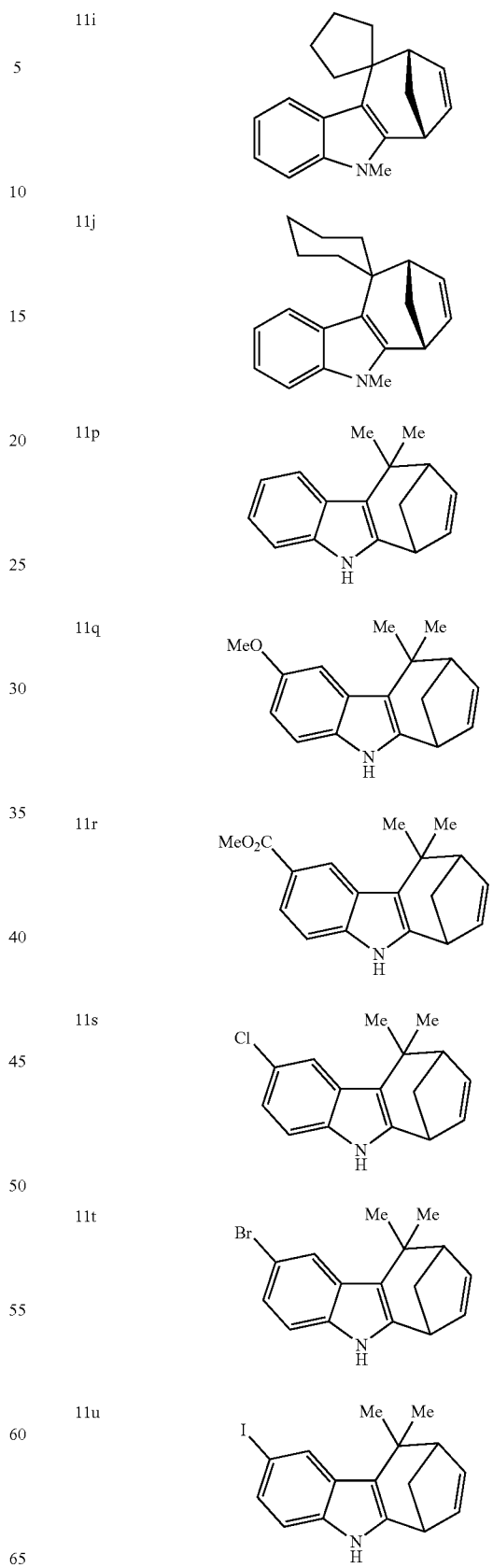

| | | | | |
|---|---|---|---|---|
| 11v | 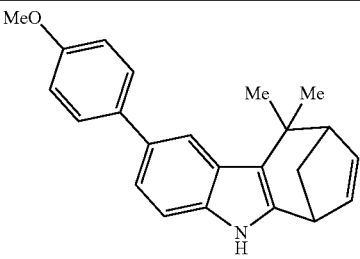 | | 11y | 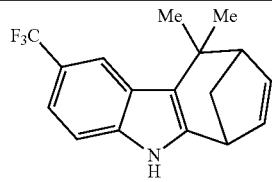 |
| 11w | 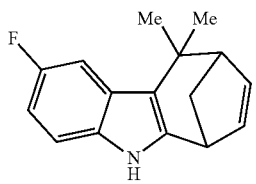 [SMILES: CC1(C)c2c([nH]c3ccc(I)cc23)C2C=CC1C2] | | 11p | 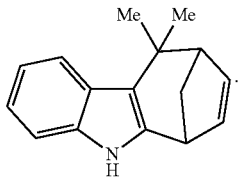 |
| 11x | 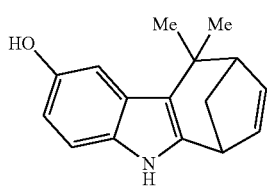 [SMILES: CC1(C)c2c([nH]c3ccc(O)cc23)C2C=CC1C2] | | | |
21. A method for stimulating the secretion and/or production of glucagon-like peptide-1 (GLP-1) or inhibiting the activity of Calcitonin Gene-Related Peptide (CGRP) receptor comprising contacting a cell with a compound of claim 13 so that the secretion and/or production of GLP-1 is stimulated or the activity of the CGRP receptor is inhibited.
* * * * *